(12) United States Patent
Washburn et al.

(10) Patent No.: US 7,342,127 B2
(45) Date of Patent: Mar. 11, 2008

(54) SUBSTITUTED ANILIDE LIGANDS FOR THE THYROID RECEPTOR

(75) Inventors: William N. Washburn, Titusville, NJ (US); Wei Meng, Pennington, NJ (US); Denis E. Ryono, Princeton, NJ (US); Bruce A. Ellsworth, Princeton, NJ (US); Thomas Ericsson, Sodertalje (SE); Mahmoud Rahimi-Ghadim, Stockholm (SE); Neeraj Garg, Tumba (SE); Johan Malm, Trangsund (SE)

(73) Assignees: Bristol-Myers Squibb Company, Princeton, NJ (US); Karo Bio AB, Huddinge (SE)

( * ) Notice: Subject to any disclaimer, the term of this patent is extended or adjusted under 35 U.S.C. 154(b) by 680 days.

(21) Appl. No.: 10/763,878

(22) Filed: Jan. 23, 2004

(65) Prior Publication Data

US 2004/0180940 A1    Sep. 16, 2004

Related U.S. Application Data

(60) Provisional application No. 60/442,421, filed on Jan. 24, 2003.

(51) Int. Cl.
C07C 54/00 (2006.01)
C07C 315/00 (2006.01)
C07C 229/00 (2006.01)
A01N 37/12 (2006.01)

(52) U.S. Cl. .................... 562/471; 562/430; 562/442; 562/443; 514/534

(58) Field of Classification Search ................ 564/192, 564/161, 171; 560/9, 19, 24, 55, 61; 562/426, 562/427, 433, 442, 465

See application file for complete search history.

(56) References Cited

U.S. PATENT DOCUMENTS

| | | |
|---|---|---|
| 3,239,345 A | 3/1966 | Hodge et al. |
| 3,983,140 A | 9/1976 | Endo et al. |
| 4,027,009 A | 5/1977 | Grier et al. |
| 4,036,979 A | 7/1977 | Asato |
| 4,231,938 A | 11/1980 | Monaghan et al. |
| 4,346,227 A | 8/1982 | Terahara et al. |
| 4,379,785 A | 4/1983 | Weyer et al. |
| 4,411,890 A | 10/1983 | Momany |
| 4,448,784 A | 5/1984 | Glamkowski et al. |
| 4,450,171 A | 5/1984 | Hoffman et al. |
| 4,499,289 A | 2/1985 | Baran et al. |
| 4,572,912 A | 2/1986 | Yoshioka et al. |
| 4,613,610 A | 9/1986 | Wareing |
| 4,639,436 A | 1/1987 | Junge et al. |
| 4,647,576 A | 3/1987 | Hoefle et al. |
| 4,681,893 A | 7/1987 | Roth |
| 4,686,237 A | 8/1987 | Anderson |
| 4,759,923 A | 7/1988 | Buntin et al. |
| 4,871,721 A | 10/1989 | Biller |
| 4,904,769 A | 2/1990 | Rauenbusch |
| 4,924,024 A | 5/1990 | Biller |
| 5,006,530 A | 4/1991 | Angerbauer et al. |
| 5,011,930 A | 4/1991 | Fujikawa et al. |
| 5,177,080 A | 1/1993 | Angerbauer et al. |
| 5,260,440 A | 11/1993 | Hirai et al. |
| 5,273,995 A | 12/1993 | Roth |
| 5,346,701 A | 9/1994 | Heiber et al. |
| 5,354,772 A | 10/1994 | Kathawala |
| 5,385,929 A | 1/1995 | Bjorge et al. |
| 5,401,772 A | 3/1995 | Yokoyama et al. |
| 5,488,064 A | 1/1996 | Sher |
| 5,491,134 A | 2/1996 | Sher et al. |
| 5,506,219 A | 4/1996 | Robl |
| 5,541,204 A | 7/1996 | Sher et al. |
| 5,594,016 A | 1/1997 | Ueno et al. |
| 5,595,872 A | 1/1997 | Wetterau, II et al. |

(Continued)

FOREIGN PATENT DOCUMENTS

EP    0 221 025    5/1987

(Continued)

OTHER PUBLICATIONS

Silverman, Organic Chemistry of Drug Design (1992) pp. 19-23.*

(Continued)

*Primary Examiner*—Karl Puttlitz
(74) *Attorney, Agent, or Firm*—Maureen Gibbons

(57) ABSTRACT

Novel thyroid receptor ligands are provided having the general formula I

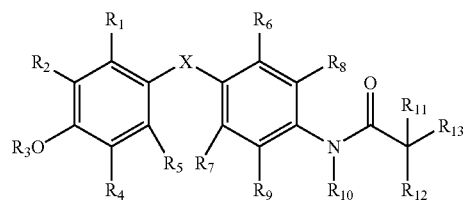

wherein
X, $R_1$, $R_2$, $R_3$, $R_4$, $R_5$, $R_6$, $R_7$, $R_8$, $R_9$, $R_{10}$, $R_{11}$, $R_{12}$ and $R_{13}$ are as defined herein.

In addition, a method is provided for preventing, inhibiting or treating diseases or disorders associated with metabolic dysfunction or which are dependent upon the expression of a $T_3$ regulated gene, wherein a compound as described above is administered in a therapeutically effective amount.

23 Claims, No Drawings

U.S. PATENT DOCUMENTS

| | | | |
|---|---|---|---|
| 5,612,359 | A | 3/1997 | Murugesan |
| 5,614,492 | A | 3/1997 | Habener |
| 5,631,224 | A | 5/1997 | Efendic et al. |
| 5,686,104 | A | 11/1997 | Mills et al. |
| 5,691,322 | A | 11/1997 | Robl |
| 5,712,279 | A | 1/1998 | Biller et al. |
| 5,712,396 | A | 1/1998 | Magnin et al. |
| 5,739,135 | A | 4/1998 | Biller et al. |
| 5,753,675 | A | 5/1998 | Wattanasin |
| 5,760,246 | A | 6/1998 | Biller et al. |
| 5,770,615 | A | 6/1998 | Cheng et al. |
| 5,776,983 | A | 7/1998 | Washburn et al. |
| 5,827,875 | A | 10/1998 | Dickson, Jr. et al. |
| 5,885,983 | A | 3/1999 | Biller et al. |
| 5,962,440 | A | 10/1999 | Sulsky |
| 6,043,265 | A | 3/2000 | Murugesan et al. |
| 6,090,854 | A | 7/2000 | Epperson |
| 6,184,231 | B1 | 2/2001 | Hewawasam et al. |
| 6,664,291 | B2 * | 12/2003 | Chiang et al. .............. 514/533 |

FOREIGN PATENT DOCUMENTS

| | | |
|---|---|---|
| EP | 0 142 146 | 8/1988 |
| EP | 0 773 226 | 1/1999 |
| EP | 0 684 254 | 3/1999 |
| EP | 0 598 359 | 6/2000 |
| EP | 0 850 948 | 4/2002 |
| EP | 1 297 833 | 4/2003 |
| FR | 2 596 393 | 10/1987 |
| GB | 2 205 837 | 12/1988 |
| JP | 8-27006 | 1/1996 |
| JP | 9-124684 | 5/1997 |
| JP | 9-124685 | 5/1997 |
| JP | 9-188625 | 7/1997 |
| JP | 10-245391 | 9/1998 |
| WO | WO 86/03488 | 6/1986 |
| WO | WO 86/07054 | 12/1986 |
| WO | WO 89/07110 | 8/1989 |
| WO | WO 89/07111 | 8/1989 |
| WO | WO 93/04081 | 3/1993 |
| WO | WO 96/38144 | 12/1996 |
| WO | WO 97/12613 | 4/1997 |
| WO | WO 97/12615 | 4/1997 |
| WO | WO 97/21993 | 6/1997 |
| WO | WO 99/00353 | 1/1999 |
| WO | WO 99/38501 | 8/1999 |
| WO | WO 99/46272 | 9/1999 |
| WO | WO 99/61431 | 12/1999 |
| WO | WO 99/67278 | 12/1999 |
| WO | WO 99/67279 | 12/1999 |
| WO | WO 00/01389 | 1/2000 |
| WO | 01/60784 * | 8/2001 |
| WO | WO 01/60784 | 8/2001 |
| WO | WO 01/70687 | 9/2001 |
| WO | WO 01/72692 | 10/2001 |
| WO | WO 01/85670 | 11/2001 |
| WO | WO 01/90053 | 11/2001 |
| WO | WO 01/94293 | 12/2001 |
| WO | WO 02/051805 | 7/2002 |
| WO | WO 02/062780 | 8/2002 |
| WO | WO 02/090344 | 11/2002 |
| WO | WO 02/094319 | 11/2002 |
| WO | WO 2004/018421 | 3/2004 |

OTHER PUBLICATIONS

CAS online citation of [retrieved Feb. 21, 2007] from STN, Columbus, OH, USA, No. 2001:730688.*

Ashworth, D.M. et al., "2-Cyanopyrrolidides as Potent, Stable Inhibitors of Dipeptidyl Peptidase IV", Bioorganic & Medicinial Chemistry Letters, vol. 6, No. 10, pp. 1163-1166 (1996).

Ashworth, D.M. et al., "4-Cyanothiazolidides as Very Potent, Stable Inhibitors of Dipeptidyl Peptidase IV", Bioorganic & Medicinial Chemistry Letters, vol. 6, No. 22, pp. 2745-2748 (1996).

Biller, S.A. et al., "Isoprenoid (Phosphinylmethyl)phosphonates as Inhibitors of Squalene Synthetase", Journal of Medicinal Chemistry, vol. 31, No. 10, pp. 1869-1871 (1988).

Biller, S.A. et al., "Squalene Synthase Inhibitors", Current Pharmaceutical Design, vol. 2, No. 1, pp. 1-40 (1996).

Bundgaard, H., Chapter 5: "Design and Application of Prodrugs", A Textbook of Drug Design and Development, Harwood Academic Publishers, publ., Krogsgaard-Larsen, P. et al., eds., pp. 113-191 (1991).

Bundgaard, H., ed., Design of Prodrugs, Elsevier Science Publishers B.V., publ. (1985) (table of contents).

Capson, T.L., "Synthesis and Evaluation of Ammonium Analogs of Carbocationic Intermediates in Squalene Biosynthesis", dissertation, Department of Medicinal Chemistry, University of Utah, pp. iv-v, Table of Contents, 16-17, 40-43, 48-51, Summary (Jun. 1987).

Chakrabartty, S.K., Chapter V: "Alkaline Hypohalite Oxidations", Oxidation in Organic Chemistry, Part C, Academic Press, Inc., publ., Trahanovsky, W.S., ed., pp. 343-370 (1978).

Chan, D.M.T. et al., "New N- and O-Arylations with Phenylboronic Acids and Cupric Acetate", Tetrahedron Letters, vol. 39, pp. 2933-2936 (1998).

Chiellini, G. et al., "A high-affinity subtype-selective agonist ligand for the thyroid hormone receptor", Chemistry & Biology, vol. 5, No. 6, pp. 299-306 (1998).

Corey, E.J. et al., "Application of Unreactive Analogs of Terpenoid Pyrophosphates to Studies of Multistep Biosynthesis. Demonstration That 'Presqualene Pyrophosphate' Is an Essential Intermediate on the Path to Squalene", J. Am. Chem. Soc., vol. 98, No. 5, pp. 1291-1293 (1976).

Cornicelli, J.A. et al., "15-Lipoxygenase and Its Inhibition: A Novel Therapeutic Target for Vascular Disease", Current Pharmaceutical Design, vol. 5, No. 1, pp. 11-20 (1999).

Couladouros, E.A. et al., "A general synthetic route towards bastadins. Part 1: Synthesis of the eastern part of bastadins 4-16", Tetrahedron Letters, vol. 40, pp. 7023-7026 (1999).

Dibbo, A. et al., "The Synthesis of Thyroxine and Related Compounds. Part XVII. The Preparation of Some Additional Compounds related to Thyroxine", J. Chem. Soc., pp. 2890-2902 (1961).

Driver, M.S. et al., "A Second-Generation Catalyst for Aryl Halide Amination: Mixed Secondary Amines from Aryl Halides and Primary Amines Catalyzed by $(DPPF)PdCl_2$", J. Am. Chem. Soc., vol. 118, No. 30, pp. 7217-7218 (1996).

Edwards, J.P. et al., "Nonsteroidal Androgen Receptor Agonists Based on 4-(trifluoromethyl)-2H-pyrano[3,2-g]quinolin-2-one", Bioorganic & Medicinal Chemistry Letters, vol. 9, pp. 1003-1008 (1999).

Evans, D.A. et al., "Synthesis of Diaryl Ethers through the Copper-Promoted Arylation of Phenols with Arylboronic Acids. An Expedient Synthesis of Thyroxine", Tetrahedron Letters, vol. 39, pp. 2937-2940 (1998).

Frost, C.G. et al., "Recent developments in aromatic heteroatom coupling reactions", J. Chem. Soc., Perkin Trans. 1, pp. 2615-2623 (1998).

Ghiselli, G., "The Pharmacological Profile of FCE 27677: A Novel ACAT Inhibitor with Potent Hypolipidemic Activity Mediated by Selective Suppression of the Hepatic Secretion of ApoB-100-Containing Lipoprotein", Cardiovascular Drug Reviews, vol. 16, No. 1, pp. 16-30 (1998).

Greene, T.W. et al., Protective Groups in Organic Synthesis, Third Edition, John Wiley & Sons, Inc., publ. (1999) (table of contents).

Guo, Z.-W. et al., "Enzymatic Oxidative Phenolic Coupling", J. Org. Chem., vol. 62, No. 20, pp. 6700-6701 (1997).

Hamann, L.G. et al., "Discovery of a Potent, Orally Active, Nonsteroidal Androgen Receptor Agonist: 4-Ethyl-1,2,3,4-tetrahydro-6-(trifluoromethyl)-8-pyridono[5,6-g]-quinoline (LG121071)", J. Med. Chem., vol. 42, No. 2, pp. 210-212 (1999).

Hara, S., "Ileal $Na^+$/bile acid cotransporter inhibitors", Drugs of the Future, vol. 24, No. 4, pp. 425-430 (1999).

Harrington, C.R., "Synthesis of a Sulphur-containing Analogue of Thyroxine", Biochem. J., vol. 43, pp. 434-437 (1948).

Hickey, D.M.B. et al., "Synthesis of Thyroid Hormone Analogues. Part 2. Oxidative Coupling Approach to SK&F L-94901", J. Chem. Soc. Perkin Trans. I, pp. 3097-3102 (1988).

Hickey, D.M.B. et al., "Synthesis of Thyroid Hormone Analogues. Part 3. Iodonium Salt Approaches to SK&F L-94901", J. Chem. Soc. Perkin Trans. I, pp. 3103-3111 (1988).

Hongu, M. et al., "$Na^+$-Glucose Cotransporter Inhibitors as Antidiabetic Agents. II. Synthesis and Structure-Activity Relationships of 4'-Dehydroxyphlorizin Derivatives", Chem. Pharm. Bull., vol. 46, No. 1, pp. 22-33 (1998).

Hongu, M. et al., "$Na^+$-Glucose Cotransporter Inhibitors as Antidiabetic Agents. III. Synthesis and Pharmacological Properties of 4'-Dehydroxyphlorizin Derivatives Modified at the OH Groups of the Glucose Moiety", Chem. Pharm. Bull., vol. 46, No. 10, pp. 1545-1555 (1998).

Horner, L. et al., "Die Synthese brücken-analoger Thyroninverbindungen", Chemische Berichte, vol. 85, pp. 520-530 (1952).

Hughes, T.E. et al., "NVP-DPP728: (1-[[[2- (5-Cyanopyridin-2-yl)amino]ethyl]acetyl]-2-cyano-(S)-pyrrolidine), a Slow-Binding Inhibitor of Dipeptidyl Peptidase IV", Biochemistry, vol. 38, No. 36, pp. 11597-11603 (1999).

Jain, G.K. et al., "Punarnavoside: A New Antifibrinolytic Agent from *Boerhaavia diffusa* Linn", Indian Journal of Chemistry, vol. 28B, pp. 163-166 (1989).

Johannsson, G. et al., "Growth Hormone Treatment of Abdominally Obese Men Reduces Abdominal Fat Mass, Improves Glucose and Lipoprotein Metabolism, and Reduces Diastolic Blood Pressure", Journal of Clinical Endocrinology and Metabolism, vol. 82, No. 3, pp. 727-734 (1997).

Jones, R.M. et al., "A Mild Anionic Method for Generating *o*-Quinone Methides: Facile Preparations of *Ortho*-Functionalized Phenols", J. Org. Chem. vol. 66, No. 10, pp. 3435-3441 (2001).

Kalinin, A.V. et al., "The Directed Ortho Metalation-Ullmann Connection. A New Cu(I)-Catalyzed Variant for the Synthesis of Substituted Diaryl Ethers", J. Org. Chem. vol. 64, No. 9, pp. 2986-2987 (1999).

Kämmerer, H. et al., "Versuche zur Umsetzung von Methylendiphenolen mit Glucosederivaten und zur Kondensation von *O*-Phenylglucosidderivaten", Makromol. Chem., vol. 182, pp. 1351-1361 (1981).

Krause, B.R. et al., Chapter 6: "ACAT Inhibitors: Physiologic Mechanisms for Hypolipidemic and Anti-Atherosclerotic Activities in Experimental Animals", Inflammation: Mediators Pathways, CRC Press Inc., publ., Ruffolo, Jr., R.R. et al., eds., pp. 173-198 (1995).

Leeson, P.D. et al., "Synthesis of Thyroid Hormone Analogues. Part 1. Preparation of 3'-Heteroarylmethyl-3,5-di-iodo-L-thyronines *via* Phenol-Dinitrophenol Condensation and Relationships between Structure and Selective Thyromimetic Activity", J. Chem. Soc. Perkin Trans. I, pp. 3085-3096 (1988).

Lévai, A. et al., "Circular Dichroism, LXVI: Chiroptical Properties of Some Mono- and Polysubstituted Phenyl Glycosides", Acta Chim. (Budapest), vol. 84, No. 1, pp. 99-107 (1975).

Marcoux, J.-F. et al., "A General Copper-Catalyzed Synthesis of Diaryl Ethers", vol. 119, No. 43, pp. 10539-10540 (1997).

McClard, R.W. et al., "Novel Phosphonylphosphinyl (P-C-P-C-) Analogues of Biochemically Interesting Diphosphates. Syntheses and Properties of P-C-P-C- Analogues of Isopentenyl Diphosphate and Dimethylallyl Diphosphate", J. Am. Chem. Soc., vol. 109, pp. 5544-5545 (1987).

Murakami, K. et al., "A Novel Insulin Sensitizer Acts as a Coligand for Peroxisome Proliferator-Activated Receptor-α (PPAR-α) and PPAR-γ: Effect of PPAR-α Activation on Abnormal Lipid Metabolism in Liver of Zucker Fatty Rats", Diabetes, vol. 47, pp. 1841-1847 (1998).

Nicolosi, R.J. et al., "The ACAT Inhibitor, CI-1011 is effective in the prevention and regression of aortic fatty streak area in hamsters", Atherosclerosis, vol. 137, pp. 77-85 (1998).

Ortiz de Montellano, P.R. et al., "Inhibition of Squalene Synthetase by Farnesyl Pyrophosphate Analogues", Journal of Medicinal Chemistry, vol. 20, No. 2, pp. 243-249 (1977).

Rosenblum, S.B. et al., "Discovery of 1-(4-Fluorophenyl)-(3*R*)-[3-(4-fluorophenyl)-(3*S*)-hydroxypropyl]-(4*S*)-(4-hydroxyphenyl)-2-azetidinone (SCH 58235): A Designed, Potent, Orally Active Inhibitor of Cholesterol Absorption", J. Med. Chem., vol. 41, No. 6, pp. 973-980 (1998).

Ryan, M.J. et al., "HK-2: An immortalized proximal tubule epithelial cell line from normal adult human kidney", Kidney International, vol. 45, pp. 48-57 (1994).

Salamonczyk, G.M. et al., "A Concise Synthesis of Thyroxine ($T_4$) and 3,5,3'-Triiodo-L-thyronine ($T_3$)", Tetrahedron Letters, vol. 38, No. 40, pp. 6965-6968 (1997).

Salisbury, B.G. et al., "Hypocholesterolemic activity of a novel inhibitor of cholesterol absorption, SCH 48461", Atherosclerosis, vol. 115, pp. 45-63 (1995).

Sendobry, S.M. et al., "Attenuation of diet-induced atherosclerosis in rabbits with a highly selective 15-lipoxygenase inhibitor lacking significant antioxidant properties", British Journal of Pharmacology, vol. 120, pp. 1199-1206 (1997).

Shine, H.J., Aromatic Rearrangements, Elsevier Publishing Company, publ., pp. 72-82, 364-368 (1967).

Sliskovic, D.R. et al., "ACAT Inhibitors: Potential Anti-atherosclerotic Agents", Current Medicinal Chemistry, vol. 1, No. 3, pp. 204-225 (1994).

Smith, C. et al., "RP 73163: A Bioavailable Alkylsulphinyl-Diphenylimidazole ACAT Inhibitor", Bioorganic & Medicinal Chemistry Letters, vol. 6, No. 1, pp. 47-50 (1996).

Sorbera, L.A. et al., "Avasimibe: Treatment of Lipoprotein Disorders—ACAT Inhibitor", Drugs of Future, vol. 24, No. 1, pp. 9-15 (1999).

Stout, D.M., "Inhibitors of Acyl-CoA:Cholesterol *O*-Acyl Transferase (ACAT) as Hypocholesterolemic Agents. 6. The First Water-Soluble ACAT Inhibitor with Lipid-Regulating Activity, etc.", Chemtracts-Organic Chemistry, vol. 8, pp. 359-362 (1995).

Takeda, K. et al., "Recessive Inheritance of Thyroid Hormone Resistance Caused by Complete Deletion of the Protein-Coding Region of the Thyroid Hormone Receptor-β Gene", Journal of Clinical Endocrinology and Metabolism, vol. 74, No. 1, pp. 49-55 (1992).

Tsujihara, K. et al., "$Na^+$-Glucose Cotransporter Inhibitors as Antidiabetics. I. Synthesis and Pharmacological Properties of 4'-Dehydroxyphlorizin Derivatives Based on a New Concept", Chem. Pharm. Bull., vol. 44, No. 6, pp. 1174-1180 (1996).

Wermuth, C.G. et al., Chapter 31: "Designing Prodrugs and Bioprecursors I: Carrier Prodrugs", The Practice of Medicinal Chemistry, Academic Press, publ., Wermuth, C.G., ed., pp. 671-696 (1996).

Wolfe, J.P. et al., "An Improved Catalyst System for Aromatic Carbon-Nitrogen Bond Formation: The Possible Involvement of Bis(Phosphine) Palladium Complexes as Key Intermediates", J. Am. Chem. Soc., vol. 118, No. 30, pp. 7215-7216 (1996).

Yamada, M. et al., "A Potent Dipeptide Inhibitor of Dipeptidyl Peptidase IV", Bioorganic & Medicinal Chemistry Letters, vol. 8, pp. 1537-1540 (1998).

* cited by examiner

SUBSTITUTED ANILIDE LIGANDS FOR THE THYROID RECEPTOR

CROSS-REFERENCE TO RELATED APPLICATION

This application claims the benefit of U.S. Provisional Application No. 60/442,421, filed Jan. 24, 2003, which is incorporated herein by reference.

FIELD OF THE INVENTION

This invention relates to novel compounds which are thyroid receptor ligands, and to methods of preparing such compounds and to methods for using such compounds such as in the regulation of metabolism.

BACKGROUND OF THE INVENTION

While the extensive role of thyroid hormones in regulating metabolism in humans is well recognized, the discovery and development of new specific drugs for improving the treatment of hyperthyroidism and hypothyroidism has been slow. This has also limited the development of thyroid agonists and antagonists for treatment of other important clinical indications, such as hypercholesterolemia, obesity and cardiac arrhythmias.

Thyroid hormones affect the metabolism of virtually every cell of the body. At normal levels, these hormones maintain body weight, metabolic rate, body temperature and mood, and influence blood levels of serum low density lipoprotein (LDL). Thus, in hypothyroidism there is weight gain, high levels of LDL cholesterol, and depression. In hyperthyroidism, these hormones lead to weight loss, hypermetabolism, lowering of serum LDL levels, cardiac arrhythmias, heart failure, muscle weakness, bone loss in postmenopausal women, and anxiety.

Thyroid hormones are currently used primarily as replacement therapy for patients with hypothyroidism. Therapy with L-thyroxine returns metabolic functions to normal and can easily be monitored with routine serum measurements of levels of thyroid-stimulating hormone (TSH), thyroxine (3,5,3',5'-tetraiodo-L-thyronine, or $T_4$) and triiodothyronine (3,5,3'-triiodo-L-thyronine, or $T_3$). However, replacement therapy, particularly in older individuals, may be restricted by certain detrimental effects from thyroid hormones.

In addition, some effects of thyroid hormones may be therapeutically useful in non-thyroid disorders if adverse effects can be minimized or eliminated. These potentially useful influences include weight reduction, lowering of serum LDL levels, amelioration of depression and stimulation of bone formation. Prior attempts to utilize thyroid hormones pharmacologically to treat these disorders have been limited by manifestations of hyperthyroidism, and in particular by cardiovascular toxicity.

Furthermore, useful thyroid agonist drugs should minimize the potential for undesired consequences due to locally induced hypothyroidism, i.e. sub-normal levels of thyroid hormone activity in certain tissues or organs. This can arise because increased circulating thyroid hormone agonist concentrations may cause the pituitary to suppress the secretion of thyroid stimulating hormone (TSH), thereby reducing thyroid hormone synthesis by the thyroid gland (negative feedback control). Since endogenous thyroid hormone levels are reduced, localized hypothyroidism can result wherever the administered thyroid agonist drug fails to compensate for the reduction in endogenous hormone levels in specific tissues. For example, if the thyroid agonist drug does not penetrate the blood-brain barrier, the effects of TSH suppression can lead to CNS hypothyroidism and associated risks such as depression.

Development of specific and selective thyroid hormone receptor ligands, particularly agonists of the thyroid hormone receptor could lead to specific therapies for these common disorders, while avoiding the cardiovascular and other toxicity of native thyroid hormones. Tissue-selective thyroid hormone agonists may be obtained by selective tissue uptake or extrusion, topical or local delivery, targeting to cells through other ligands attached to the agonist and targeting receptor subtypes. Tissue selectivity can also be achieved by selective regulation of thyroid hormone responsive genes in a tissue specific manner.

Accordingly, the discovery of compounds that are thyroid hormone receptor ligands, particularly selective agonists of the thyroid hormone receptor, may demonstrate a utility for the treatment or prevention of diseases or disorders associated with thyroid hormone activity, for example: (1) replacement therapy in elderly subjects with hypothyroidism who are at risk for cardiovascular complications; (2) replacement therapy in elderly subjects with subclinical hypothyroidism who are at risk for cardiovascular complications; (3) obesity; (4) hypercholesterolemia due to elevations of plasma LDL levels; (5) depression; and (6) osteoporosis in combination with a bone resorption inhibitor.

SUMMARY OF THE INVENTION

In accordance with the present invention, compounds are provided which are thyroid hormone receptor ligands, and have the general formula I

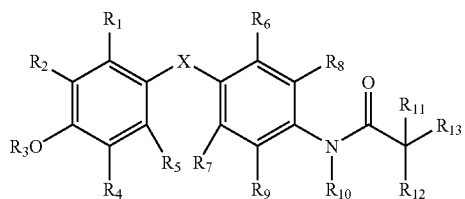

I

Wherein:

X is selected from oxygen (—O—), selenium (—Se—), sulfur (—S—), sulfenyl (SO), sulfonyl ($SO_2$), carbonyl (—CO—), methylene (—$CH_2$—) and —NH—;

$R_1$ is selected from hydrogen, halogen, $CF_3$ and $C_1$ to $C_6$ alkyl;

$R_2$ is selected from halogen, $CF_3$, $C_1$ to $C_6$ alkyl, $C_2$ to $C_6$ alkenyl, $C_2$ to $C_6$ alkynyl, $C_3$ to $C_7$ cycloalkyl, $C_4$ to $C_7$ cycloalkenyl, aryl, heteroaryl, alkoxy, aryloxy, $COR_{14}$, $CR_{14}(OR_{10})R_{15}$, heteroaryloxy, arylalkoxy, cycloalkoxy, $N(R_{14})COR_{15}$, $CO(NR_{14}R_{15})$, $N(R_{14})SO_2R_{16}$, $SO_2(NR_{14}R_{15})$, $SR_{16}$, $SOR_{16}$, $SO_2R_{16}$, and $CH_2NR_{14}R_{15}$;

$R_3$ is selected from hydrogen, alkyl, benzyl, aroyl and alkanoyl;

$R_4$ is halogen or alkyl;

$R_5$ is hydrogen, halogen or alkyl;

$R_6$ and $R_7$ are each independently selected from hydrogen, halogen, cyano, $C_1$ to $C_4$ alkyl and $C_3$ to $C_6$ cycloalkyl, where at least one of $R_6$ and $R_7$ is not hydrogen;

$R_8$ and $R_9$ are each independently selected from hydrogen, halogen, alkoxy, hydroxy(—OH), cyano, $CF_3$ and alkyl, where at least one of $R_6$ and $R_7$ is not hydrogen;

provided that no more than one of $R_6$, $R_7$, $R_8$ and $R_9$ is hydrogen;

$R_{10}$ for each occurrence is independently selected from hydrogen or alkyl;

$R_{11}$ is $CO_2R_{14}$;

$R_{12}$ and $R_{13}$ are each independently selected from hydrogen, halogen and alkyl;

$R_{14}$ and $R_{15}$ for each occurrence are each independently selected from hydrogen, alkyl, cycloalkyl, aryl, heteroaryl, arylalkyl and heteroarylalkyl; and $R_{16}$ for each occurrence is independently selected from selected from alkyl, cycloalkyl, aryl, heteroaryl, arylalkyl and heteroarylalkyl.

The definition of formula I above includes all prodrugesters, stereoisomers and pharmaceutically acceptable salts of formula I.

The compounds of formula I are thyroid hormone receptor ligands and include compounds which are, for example, selective agonists, partial agonists, antagonists or partial antagonists of the thyroid receptor. Preferably, the compounds of formula I possess activity as agonists of the thyroid receptor and may be used in the treatment of diseases or disorders associated with thyroid receptor activity. In particular, the compounds of formula I may be used in the treatment of diseases or disorders associated with metabolic dysfunction or which are dependent upon the expression of a $T_3$ regulated gene, such as obesity, hypercholesterolemia, atherosclerosis, cardiac arrhythmias, depression, osteoporosis, hypothyroidism, goiter, thyroid cancer, glaucoma, skin disorders or diseases and congestive heart failure.

The present invention provides for compounds of formula I, pharmaceutical compositions employing such compounds and for methods of using such compounds. In particular, the present invention provides for a pharmaceutical composition comprising a therapeutically effective amount of a compound of formula I, alone or in combination with a pharmaceutically acceptable carrier.

Further, in accordance with the present invention, a method is provided for preventing, inhibiting or treating the progression or onset of diseases or disorders associated with the thyroid receptor, such as the diseases or disorders defined above and hereinafter, wherein a therapeutically effective amount of a compound of formula I is administered to a mammalian, i.e., human patient in need of treatment.

The compounds of the invention can be used alone, in combination with other compounds of the present invention, or in combination with one or more other agent(s) active in the therapeutic areas described herein.

In addition, a method is provided for preventing, inhibiting or treating the diseases as defined above and hereinafter, wherein a therapeutically effective amount of a combination of a compound of formula I and another compound of the invention and/or another type of therapeutic agent, is administered to a mammalian patient in need of treatment.

DETAILED DESCRIPTION OF THE INVENTION

[1] Thus, in a first embodiment, the present invention provides for a compound of the formula I

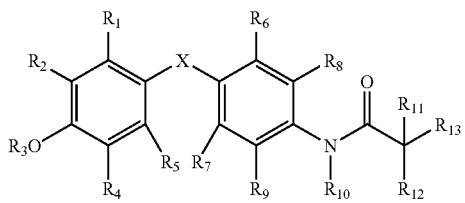

wherein:

X is selected from oxygen (—O—), selenium (—Se—), sulfur (—S—), sulfenyl (SO), sulfonyl ($SO_2$), carbonyl (—CO), methylene (—$CH_2$—) and —NH—;

$R_1$ is selected from hydrogen, halogen, $CF_3$ and $C_1$ to $C_6$ alkyl;

$R_2$ is selected from halogen, $CF_3$, $C_1$ to $C_6$ alkyl, $C_2$ to $C_6$ alkenyl, $C_2$ to $C_6$ alkynyl, $C_3$ to $C_7$ cycloalkyl, $C_4$ to $C_7$ cycloalkenyl, aryl, heteroaryl, alkoxy, aryloxy, $COR_{14}$, $CR_{14}(OR_{10})R_{15}$, heteroaryloxy, arylalkoxy, cycloalkoxy, $N(R_{14})COR_{15}$, $CO(NR_{14}R_{15})$, $N(R_{14})SO_2R_{16}$, $SO_2(NR_{14}R_{15})$, $SR_{16}$, $SOR_{16}$, $SO_2R_{16}$, and $CH_2NR_{14}R_{15}$;

$R_3$ is selected from hydrogen, alkyl, benzyl, aroyl and alkanoyl;

$R_4$ is halogen or alkyl;

$R_5$ is hydrogen, halogen or alkyl;

$R_6$ and $R_7$ are each independently selected from hydrogen, halogen, cyano, $C_1$ to $C_4$ alkyl and $C_3$ to $C_6$ cycloalkyl, where at least one of $R_6$ and $R_7$ is not hydrogen;

$R_8$ and $R_9$ are each independently selected from hydrogen, halogen, alkoxy, hydroxy(—OH), cyano, $CF_3$ and alkyl, where at least one of $R_6$ and $R_7$ is not hydrogen; provided that no more than one of $R_6$, $R_7$, $R_8$ and $R_9$ is hydrogen;

$R_{10}$ for each occurrence is independently selected from hydrogen or alkyl;

$R_{11}$ is $CO_2R_{14}$;

$R_{12}$ and $R_{13}$ are each independently selected from hydrogen, halogen and alkyl;

$R_{14}$ and $R_{15}$ for each occurrence are each independently selected from hydrogen, alkyl, cycloalkyl, aryl, heteroaryl, arylalkyl and heteroarylalkyl; and $R_{16}$ for each occurrence is independently selected from selected from alkyl, cycloalkyl, aryl, heteroaryl, arylalkyl and heteroarylalkyl, including all prodrugs, stereoisomers and pharmaceutically acceptable salts thereof.

[2] In a preferred embodiment, the present invention provides a compound of formula I, including all prodrugs, stereoisomers and pharmaceutically acceptable salts wherein: X is oxygen.

[3] In another preferred embodiment, the present invention provides a compound of formula I, including all prodrugs, stereoisomers and pharmaceutically acceptable salts wherein:

$R_1$ is hydrogen;

$R_2$ is $C_1$ to $C_6$ alkyl or $C_3$ to $C_7$ cycloalkyl;

$R_3$ is hydrogen;

$R_4$ is halogen or $C_1$ to $C_4$ alkyl;

$R_5$ is hydrogen;

$R_6$ and $R_7$ are independently bromo, chloro or methyl;

$R_8$ is halogen or $C_1$ to $C_4$ alkyl;

$R_9$ is hydrogen or halogen;

$R_{10}$ is hydrogen;

$R_{11}$ is carboxyl;

$R_{12}$ is hydrogen; and $R_{13}$ is hydrogen.

[4] In another preferred embodiment, the present invention provides a compound of formula I, including all prodrugs, stereoisomers and pharmaceutically acceptable salts wherein:

$R_2$ is isopropyl.

[5] In another preferred embodiment, the present invention provides a compound of formula I, including all prodrugs, stereoisomers and pharmaceutically acceptable salts wherein:

R₁ is hydrogen;
R₂ is isopropyl;
R₃ is hydrogen;
R₄ is C₁ to C₄ alkyl;
R₅ is hydrogen;
R₆ and R₇ are independently bromo, chloro or methyl;
R₈ is halogen or methyl;
R₉ is hydrogen or chloro;
R₁₀ is hydrogen;
R₁₁ is carboxyl;
R₁₂ is hydrogen; and
R₁₃ is hydrogen.

[6] In another preferred embodiment, the present invention provides a compound of formula I, including all prodrugs, stereoisomers and pharmaceutically acceptable salts wherein:
R₁ is hydrogen;
R₂ is isopropyl;
R₃ is hydrogen;
R₄ is methyl;
R₅ is hydrogen;
R₆ and R₇ are independently bromo or chloro;
R₈ is chloro or methyl;
R₉ is hydrogen;
R₁₀ is hydrogen;
R₁₁ is carboxyl;
R₁₂ is hydrogen; and
R₁₃ is hydrogen.

[7] In a more preferred embodiment, the present invention provides a compound of formula I, including all prodrugs, stereoisomers and pharmaceutically acceptable salts selected from:

[structure with R₆, R₇, R₈ substituents]

or

[structure with R₆, R₇, R₈, R₉ substituents]

or an alkyl ester thereof.

[8] In another more preferred embodiment, the present invention provides a compound of formula I, including all prodrugs, stereoisomers and pharmaceutically acceptable salts selected from:

[structure: Me, Br, Me, Br, Me substituents]

or

[structure: Me, Br, Cl, Br, Me substituents]

or

[structure: Me, Cl, Me, Cl, Me substituents]

or

[structure: Cl, Cl, Me substituents]

or

[structure with Br, Me, Br, Cl substituents]

or

[structure with Br, Cl, Br, Cl substituents]

or

[structure with Cl, Me, Cl substituents]

or

[structure with Cl, Cl, Cl, Cl substituents], or

[structure with Br, Me, Br and aldehyde group]

or

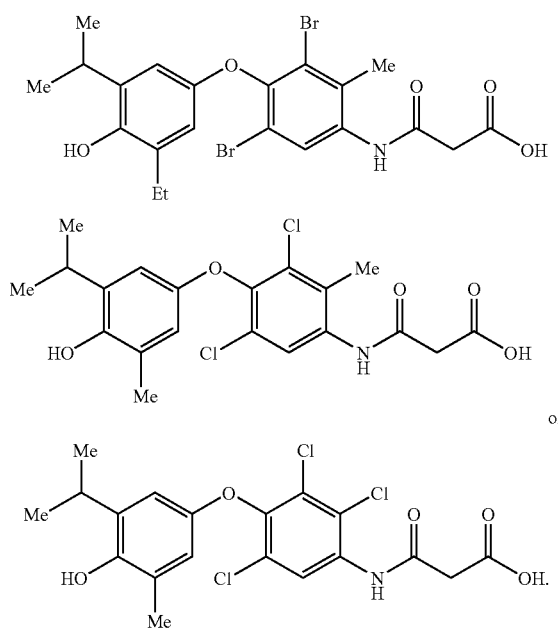

or an alkyl ester thereof.

[9] In another more preferred embodiment, the present invention provides a compound of formula I, including all prodrugs, stereoisomers and pharmaceutically acceptable salts selected from:

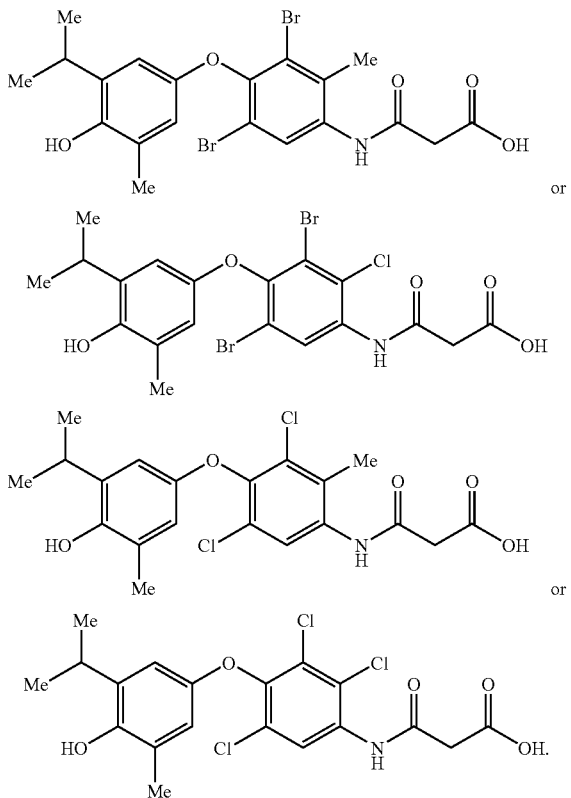

[10] In another more preferred embodiment, the present invention provides a compound of formula I, including all prodrugs, stereoisomers and pharmaceutically acceptable salts selected from:

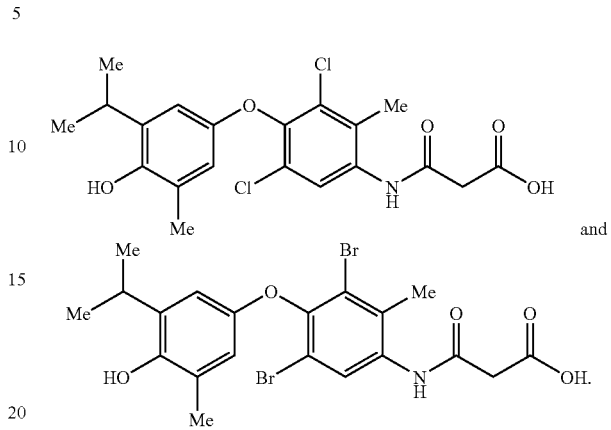

[11] In a second embodiment, the present invention provides a pharmaceutical composition comprising a compound of formula I as defined above and a pharmaceutically acceptable carrier therefor.

[12] In a preferred embodiment, the present invention provides a pharmaceutical composition as defined above further comprising at least one additional therapeutic agent selected from other compounds of formula I, anti-diabetic agents, anti-osteoporosis agents, anti-obesity agents, growth promoting agents, anti-inflammatory agents, anti-anxiety agents, anti-depressants, anti-hypertensive agents, cardiac glycosides, cholesterol/lipid lowering agents, appetite supressants, bone resorption inhibitors, thyroid mimetics, anabolic agents, anti-tumor agents and retinoids.

[13] In another preferred embodiment, the present invention provides a pharmaceutical composition as defined above wherein said additional therapeutic agent is an antidiabetic agent selected from a biguanide, a glucosidase inhibitor, a meglitinide, a sulfonylurea, a thiazolidinedione, a PPAR-alpha agonist, a PPAR-gamma agonist, a PPAR alpha/gamma dual agonist, an SGLT2 inhibitor, a glycogen phosphorylase inhibitor, an aP2 inhibitor, a glucagon-like peptide-1 (GLP-1), a dipeptidyl peptidase IV inhibitor and insulin.

[14] In another preferred embodiment, the present invention provides a pharmaceutical composition as defined above wherein said additional therapeutic agent is an antidiabetic agent selected from metformin, glyburide, glimepiride, glipyride, glipizide, chlorpropamide, gliclazide, acarbose, miglitol, troglitazone, pioglitazone, englitazone, darglitazone, rosiglitazone and insulin.

[15] In another preferred embodiment, the present invention provides a pharmaceutical composition as defined above wherein said additional therapeutic agent is an anti-obesity agent selected from an aP2 inhibitor, a PPAR gamma antagonist, a PPAR delta agonist, a beta 3 adrenergic agonist, a lipase inhibitor, a serotonin reuptake inhibitor, a cannabinoid-1 receptor antagonist and an anorectic agent.

[16] In another preferred embodiment, the present invention provides a pharmaceutical composition as defined above wherein said additional therapeutic agent is a hypolipidemic agent selected from thiazolidinedione, an MTP inhibitor, a squalene synthetase inhibitor, an HMG CoA reductase inhibitor, a fibric acid derivative, an ACAT inhibitor, a cholesterol absorption inhibitor, an ileal Na⁺/bile cotransporter inhibitor, a bile acid sequestrant and a nicotinic acid or a derivative thereof.

[17] In a third embodiment, the present invention provides a method for preventing, inhibiting or treating a disease associated with metabolic dysfunction, or which is dependent on the expression of a $T_3$ regulated gene, which comprises administering to a mammalian patient in need of treatment a therapeutically effective amount of a compound of formula I.

[18] In a preferred embodiment, the present invention provides a method as defined above for treating or delaying the progression or onset of obesity, hypercholesterolemia, atherosclerosis, depression, osteoporosis, hypothyroidism, subclinical hyperthyroidism, non-toxic goiter, reduced bone mass, density or growth, eating disorders, reduced cognitive function, thyroid cancer, glaucoma, cardiac arrhythmia, congestive heart failure or a skin disorder or disease, which comprises administering to mammalian patient in need of treatment a therapeutically effective amount of a compound of formula I.

[19] In another preferred embodiment, the present invention provides a method as defined above wherein the skin disorder or disease is dermal atrophy, post surgical bruising caused by laser resurfacing, keloids, stria, cellulite, roughened skin, actinic skin damage, lichen planus, ichtyosis, acne, psoriasis, Dernier's disease, eczema, atopic dermatitis, chloracne, pityriasis or skin scarring.

[20] In another preferred embodiment, the present invention provides a method as defined above further comprising administering, concurrently or sequentially, a therapeutically effective amount of at least one additional therapeutic agent selected from other compounds of formula I, anti-diabetic agents, anti-osteoporosis agents, anti-obesity agents, growth promoting agents, anti-inflammatory agents, anti-anxiety agents, anti-depressants, anti-hypertensive agents, cardiac glycosides, cholesterol/lipid lowering agents, appetite supressants, bone resorption inhibitors, thyroid mimetics, anabolic agents, anti-tumor agents and retinoids.

[21] In another preferred embodiment, the present invention provides a method of treating or delaying the progression or onset of a skin disorder or disease which comprises administering to a mammalian patient a therapeutically effective amount of a compound of formula I in combination with a retinoid or a vitamin D analog.

[22] In another preferred embodiment, the present invention provides a method for treating or delaying the progression or onset of obesity which comprises administering to mammalian patient in need of treatment a therapeutically effective amount of a compound of formula I.

[23] In another preferred embodiment, the present invention provides a method as described above further comprising administering, concurrently or sequentially, a therapeutically effective amount of at least one additional therapeutic agent selected from an anti-obesity agent or an appetite suppressant.

[24] In another preferred embodiment, the present invention provides a method as described above wherein said anti-obesity agent is selected from aP2 inhibitors, PPAR gamma antagonists, PPAR delta agonists, beta 3 adrenergic agonists, lipase inhibitors, serotonin (and dopamine) reuptake inhibitors, cannabinoid-1 receptor antagonists, other thyroid receptor agents and anorectic agents.

[25] In a fourth embodiment, the present invention provides a pharmaceutical composition which functions as a selective agonist of the thyroid hormone receptor comprising a compound of formula I.

The following abbreviations are employed herein:
Ph=phenyl
Bn=benzyl
t-Bu=tertiary butyl
Me=methyl
Et=ethyl
THF=tetrahydrofuran
Et$_2$O=diethyl ether
EtOAc=ethyl acetate
DMF=dimethyl formamide
MeOH=methanol
EtOH=ethanol
i-PrOH=isopropanol
HOAc or AcOH=acetic acid
TFA=trifluoroacetic acid
i-Pr$_2$NEt=diisopropylethylamine
Et$_3$N=triethylamine
DMAP=4-dimethylaminopyridine
NaBH$_4$=sodium borohydride
KOH=potassium hydroxide
NaOH=sodium hydroxide
LiOH=lithium hydroxide
K$_2$CO$_3$=potassium carbonate
NaHCO$_3$=sodium bicarbonate
Ph$_3$P=triphenylphosphine
Ar=argon
N$_2$=nitrogen
min=minute(s)
h or hr=hour(s)
L=liter
mL=milliliter
μL=microliter
g=gram(s)
mg=milligram(s)
mol=moles
mmol=millimole(s)
meq=milliequivalent
RT=room temperature
sat or sat'd=saturated
aq.=aqueous
NMR=nuclear magnetic resonance
Tf$_2$O=trifluoromethane-sulfonic anhydride
CHCl$_3$=chloroform
MeCN=acetonitrile
EDC (or EDC.HCl) or EDCI (or EDCI.HCl) or EDAC=3-ethyl-3'-(dimethylamino)propyl-carbodiimide hydrochloride (or 1-(3-dimethylaminopropyl)-3-ethylcarbodiimide hydrochloride)
HOBT or HOBT.H$_2$O=1-hydroxybenzotriazole hydrate
HOAT=1-Hydroxy-7-azabenzotriazole
TLC=thin layer chromatography
HPLC=high performance liquid chromatography
LC/MS=high performance liquid chromatography/mass spectrometry
MS or Mass Spec=mass spectrometry The following definitions apply to the terms as used throughout this specification, unless otherwise limited in specific instances.

The term "thyroid receptor ligand" as used herein is intended to cover any moiety which binds to a thyroid receptor. The ligand may act as an agonist, an antagonist, a partial agonist or a partial antagonist. Another term for "thyroid receptor ligand" is "thyromimetic".

Unless otherwise indicated, the term "alkyl" as employed herein alone or as part of another group includes both straight and branched chain hydrocarbons, containing 1 to 12 carbons (in the case of alkyl or alk), in the normal chain, preferably 1 to 4 carbons, such as methyl, ethyl, propyl, isopropyl, butyl, t-butyl, or isobutyl, pentyl, hexyl, isohexyl, heptyl, 4,4-dimethylpentyl, octyl, 2,2,4-trimethylpentyl, nonyl, decyl, undecyl, dodecyl. As defined and claimed herein, the term "alkyl" includes alkyl groups as defined above optionally substituted with 1 to 4 substituents which may halo, for example F, Br, Cl or I or $CF_3$, alkyl, alkoxy, aryl, aryloxy, aryl(aryl) or diaryl, arylalkyl, arylalkyloxy, alkenyl, alkynyl, cycloalkyl, cycloalkenyl, cycloalkylalkyl, cycloalkylalkyloxy, optionally substituted amino, hydroxy, hydroxyalkyl, acyl, oxo, alkanoyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, alkoxycarbonyl, alkylaminocarbonyl, nitro, cyano, thiol, haloalkyl, trihaloalkyl, alkylthio or carboxyl(or alkyl ester thereof).

Unless otherwise indicated, the term "cycloalkyl" as employed herein alone or as part of another group includes saturated cyclic hydrocarbon groups or partially unsaturated (containing 1 or 2 double bonds) cyclic hydrocarbon groups, containing one ring and a total of 3 to 8 carbons, preferably 3 to 6 carbons, forming the ring. As defined and claimed herein, the term "cycloalkyl" includes cycloalkyl groups as defined above optionally substituted with 1 or more substituents, such as those defined for alkyl.

The term "aryl" or "Ar" as employed herein alone or as part of another group refers to monocyclic and bicyclic aromatic groups containing 6 to 10 carbons in the ring portion (such as phenyl or naphthyl including 1-naphthyl and 2-naphthyl). As defined and claimed herein, the term "aryl" includes aryl groups as defined above optionally substituted through any available carbon atom(s) with 1 or more substitutents, such as halo, alkyl, haloalkyl, alkoxy, haloalkoxy, alkenyl, trifluoromethyl, trifluoromethoxy, alkynyl, hydroxy, amino, nitro, cyano, carboxyl(or alkyl ester thereof) or any of the other substituents described for alkyl.

Unless otherwise indicated, the term "heteroaryl" or "heteroaromatic" as used herein alone or as part of another group refers to a 5- or 6-membered aromatic ring which includes 1, 2, 3 or 4 hetero atoms such as nitrogen, oxygen, or sulfur, and such rings fused to an aryl, cycloalkyl, heteroaryl or cycloheteroalkyl ring (e.g. benzothiophenyl, indole), and includes possible N-oxides. A "substituted heteroaryl" group includes a heteroaryl optionally substituted with one or more substituents such as any of the alkyl or aryl substituents set out above. As defined and claimed herein, the term "heteroaryl" includes heteroaryl groups as defined above optionally substituted through any available carbon atom(s) with 1 or more substitutents, such as any of the substituents described for alkyl or aryl.

Unless otherwise indicated, the term "alkenyl" as used herein by itself or as part of another group refers to straight or branched chain radicals of 2 to 20 carbons, preferably 2 to 12 carbons, and more preferably 2 to 8 carbons in the normal chain, which include one or more double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like. As defined and claimed herein, the term "alkenyl" includes alkenyl groups as defined above optionally substituted through any available carbon atom(s) with 1 or more substitutents, such as any of the substituents described for alkyl or aryl.

Unless otherwise indicated, the term "alkynyl" as used herein by itself or as part of another group refers to straight or branched chain radicals of 2 to 20 carbons, preferably 2 to 12 carbons and more preferably 2 to 8 carbons in the normal chain, which include one or more triple bonds in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl,3-undecynyl, 4-dodecynyl and the like. As defined and claimed herein, the term "alkynyl" includes alkynyl groups as defined above optionally substituted through any available carbon atom(s) with 1 or more substitutents, such as any of the substituents described for alkyl or aryl.

The term "cycloalkenyl" as employed herein alone or as part of another group refers to cyclic hydrocarbons containing 3 to 12 carbons, preferably 5 to 10 carbons and 1 or 2 double bonds. Exemplary cycloalkenyl groups include cyclopentenyl, cyclohexenyl, cyclohexadienyl, and cycloheptadienyl, which may be optionally substituted as defined for cycloalkyl. As defined and claimed herein, the term "cycloalkenyl" includes cycloalkenyl groups as defined above optionally substituted through any available carbon atom(s) with 1 or more substitutents, such as any of the substituents described for alkyl or aryl.

The term "halogen" or "halo" as used herein alone or as part of another group refers to chlorine, bromine, fluorine, and iodine as well as $CF_3$, with chlorine or bromine being preferred.

The term "alkanoyl" as employed herein alone or as part of another group is alkyl linked to a carbonyl group.

The term "aroyl" as employed herein alone or as part of another group is aryl linked to a carbonyl group.

Unless otherwise indicated, the terms "alkoxy", "aryloxy" or "heteroaryloxy" as employed herein alone or as part of another group includes any of the above alkyl, aryl or heteroaryl groups linked thorough an oxygen atom.

The term "cyano," as used herein, refers to a —CN group.

The term "arylalkyl" and "heteroarylalkyl" as employed herein alone or as part of another group refer to alkyl groups as described above having an aryl or heteroaryl substituent. Representative examples of arylalkyl include, but are not limited to, benzyl, 2-phenylethyl, 3-phenylpropyl.

Unless otherwise indicated, the terms "arylalkoxy" and "cycloalkoxy" as employed herein alone or as part of another group include and aryl cycloalkyl groups linked thorough an oxygen atom.

The term "carboxylic acid" or "carboxyl", as used herein, refers to a —COOH group.

The term "benzyl" as used herein refers to —$CH_2C_6H_5$, which may optionally be substituted as defined above for alkyl.

The compounds of formula I can be present as salts, in particular pharmaceutically acceptable salts. The compounds of formula I containing at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tertbutyl, diethyl, diisopropyl, triethyl, tributyl or dimethyl-propylamine, or a mono, di or trihydroxy lower alkylamine, for example mono, di or triethanolamine. Corresponding internal salts may furthermore be formed.

Salts which are unsuitable for pharmaceutical uses but which can be employed, for example, for the isolation or purification of free compounds I or their pharmaceutically acceptable salts, are also included.

Preferred salts of the compounds of formula I which include an acid group include sodium, potassium and magnesium salts and pharmaceutically acceptable organic amines.

The compounds of formula I may also have prodrug forms. Any compound that will be converted in vivo to provide the bioactive agent (i.e., the compound of formula I) is a prodrug within the scope and spirit of the invention.

Various forms of prodrugs are well known in the art. A comprehensive description of prodrugs and prodrug derivatives may be found in:

a.) *The Practice of Medicinal Chemistry*, Camille G. Wermuth et al., Ch 31, (Academic Press, 1996);

b.) *Design of Prodrugs*, edited by H. Bundgaard, (Elsevier, 1985); and c.) *A Textbook of Drug Design and Development*, P. Krogsgaard-Larson and H. Bundgaard, eds. Ch 5, pgs 113-191 (Harwood Academic Publishers, 1991).

Preferred prodrugs include alkyl esters such as ethyl ester, or acyloxyalkyl esters such as pivaloyloxymethyl (POM).

All stereoisomers of the compounds of the instant invention are contemplated, either in admixture or in pure or substantially pure form. The compounds of the present invention can have asymmetric centers at any of the carbon atoms including any one or the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

An administration of a therapeutic agent of the invention includes administration of a therapeutically effective amount of the agent of the invention. The term "therapeutically effective amount" as used herein refers to an amount of a therapeutic agent to treat or prevent a condition treatable by administration of a composition of the invention. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration. Thus, it is not useful to specify an exact effective amount in advance.

The compounds of formula I may be prepared by the exemplary processes described in the following reaction schemes, as well as relevant published literature procedures that are used by one skilled in the art. Exemplary reagents and procedures for these reactions appear hereinafter and in the working Examples. Protection and deprotection in the Schemes below may be carried out by procedures generally known in the art (see, for example, T. W. Greene & P. G. M. Wuts, "Protecting Groups in Organic Synthesis", 3rd Edition, Wiley, 1999).

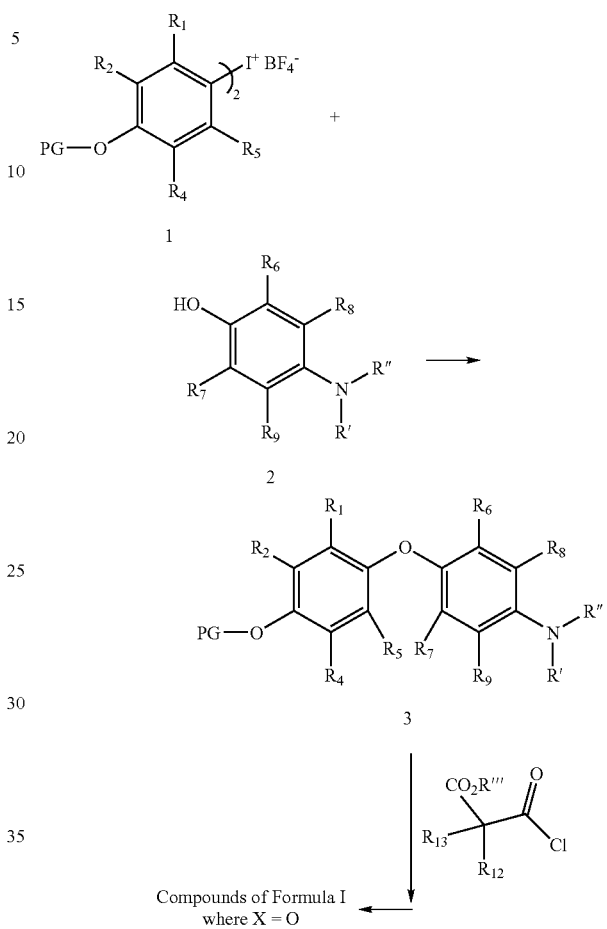

Scheme 1

Compounds of Formula I where X = O

Scheme 1 depicts a general synthetic approach to compounds of formula I for which X=O that utilizes the coupling of an appropriately substituted iodonium salt 1 to the appropriate phenol 2 to provide intermediate 3. In structure 1 and all other applicable structures contained in further schemes described below, PG refers to a protecting group appropriate for the functional group indicated (in this instance, for a phenolic oxygen). The specific protecting groups for each particular intermediate are well understood by those versed in the art (see also the reference, "Protecting Groups in Organic Synthesis", cited above). Subsequent protecting group and functional group manipulation provides the desired compounds of formula I. For example, intermediate 2 may be a nitrophenol (R' and R" are oxygen) and the resulting coupling product would be the corresponding diaryl ether nitro compound 3 where R'=R"=O. This nitro intermediate can be readily reduced to the corresponding aryl amine (see discussion below). The resulting aryl amine can then be readily acylated to provide the desired compounds of formula I (X=O). Intermediate 2 may also be a protected amino function, for example R'=$R_5$ and R"=PG. The protecting group (PG) may be carbamates such as t-butyloxycarbonyl (BOC) or benzyloxycarbonyl (CBZ), which may be later removed by acidolysis and/or hydrogenolysis under standard conditions. Acylation of the resulting aryl amine, again by means well-known to those versed in the art, provides the desired compounds of formula I. In addition, the aryl amine (intermediate 3 where R'=R"=H) resulting from reduction of a nitrobenzene coupling product can be reacted with an aldehyde in a reductive amination reaction, thus installing the group $R_5$ which comes from the aldehyde moiety. Reductive amination procedures, such as by the use of sodium cyanoborohydride or sodium triacetoxyborohydride, are well known to those skilled in the art. The resulting product can then be acylated by standard procedures to provide compounds of formula I.

The iodonium salt methodology depicted in Scheme 1 is amply described in the literature for the synthesis of thyroid hormone analogs ("Novel Thyroid Receptor Ligands and Methods, Y.-L. Li, Y. Liu, A. Hedfors, J. Malm, C. Mellin, M. Zhang, PCT Int. App. WO 9900353 A1 990107; D. M. B. Hickey et al., J. Chem. Soc. Perkin Trans. I, 3103-3111, 1988; N. Yokoyama et al., J. Med. Chem., 38, 695-707, 1995), and to diaryl ethers in general (E. A. Couladouros, V. I. Moutsos, Tetrahedron Lett., 40, 7023-7026, 1999).

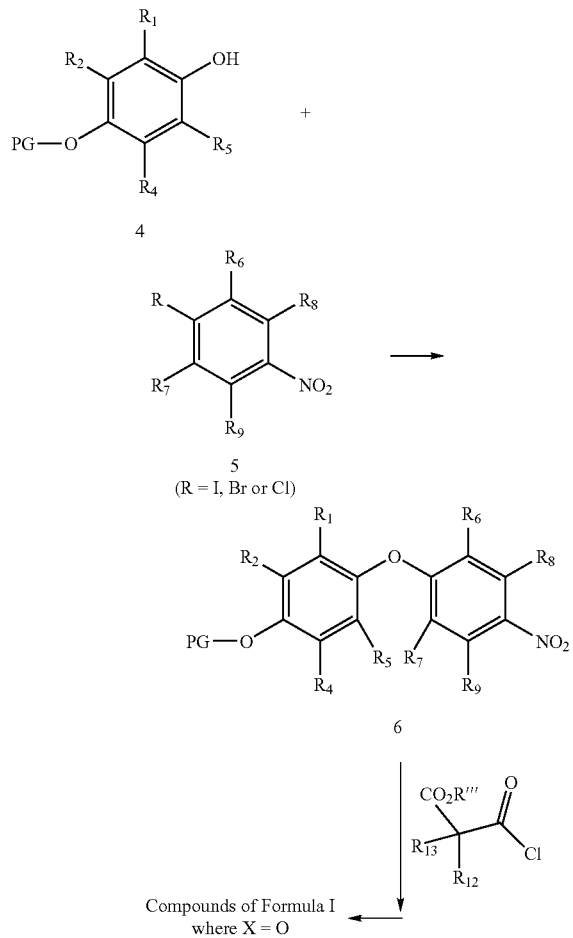

Scheme 2 depicts another general synthetic approach to compounds of formula I for which X=O in which an appropriately substituted nitrobenzene intermediate 5 is condensed with an appropriately substituted phenol 4 to provide the nitro intermediate 6. The nitro function in intermediate 6 can be reduced to an amino group by methods well known in the art, such as the use of catalytic hydrogenation in the presence of, for example, Raney nickel or palladium on charcoal catalyst, in a polar solvent such as glacial acetic acid or ethanol. Alternatively, the reduction can be accomplished using iron powder in aqueous glacial acetic acid at ambient temperatures. Subsequent protecting group and functional group manipulation provides the desired compounds of formula I.

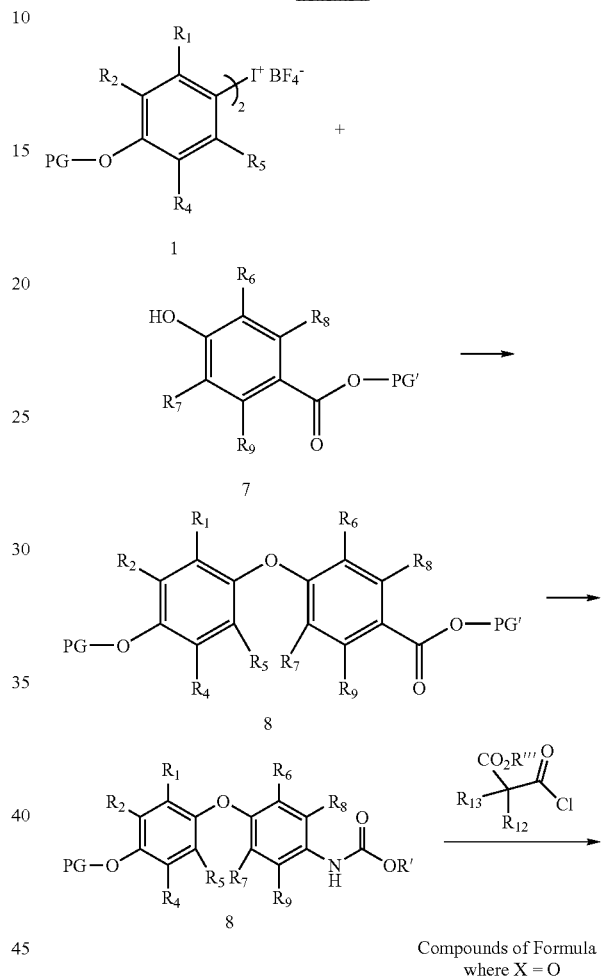

Another general approach to the synthesis of compounds of formula I in which X=O is shown in Scheme 3. In this approach, an appropriately substituted iodonium salt 1 is coupled to the appropriately substituted 4-hydroxybenzoic acid intermediate 7. The carboxyl protecting group (PG') in the resulting coupling product 8 is then removed. The resulting free carboxylic acid intermediate corresponding to 8 is then subjected to a Curtius rearrangement by the use of known reagents for that transformation such as diphenylphosphoryl azide (DPPA). The Curtius rearrangement intermediate can be trapped by either t-butanol or benzyl alcohol to give the product 9, a t-butyloxycarbonyl (BOC) or a benzyloxycarbonyl (CBZ) protected aniline, respectively. These protecting groups can be removed by methods well known in the art to give the corresponding free amine group. The amine can then be acylated to give compounds of formula I with X=O by one of any number of well-established procedures, such as acylation with a free carboxylic acid by using a coupling reagent such as dicyclohexyl carbodiimide (DCC) or (1-[3-(dimethylamino)propyl]-3-ethylcarbodiimide (EDCI). Alternatively, the free amine can be acylated using a carboxylic acid chloride derivative in the presence of an equivalent amount of a tertiary organic amine such as triethylamine or N-methyl morpholine.

With reference to the syntheses described above, the general synthesis of diaryl ethers for thyromimetics is well precedented in the literature (P. D. Leeson, J. C. Emmett, J. Chem. Perkin Trans. I, 3085-3096, 1988; N. Yokoyama et al., J. Med. Chem., 38, 695-707, 1995).

Methods applicable to the synthesis of compounds of formula I in which X=O and $R_6$ and $R_7$ are independently varied as hydrogen, halogen and alkyl are described in "Novel Thyroid Receptor Ligands and Methods, Y.-L. Li, Y. Liu, A. Hedfors, J. Malm, C. Mellin, M. Zhang, PCT Int. App. WO 9900353 A1 990107.

Further means for synthesizing compounds of formula I in which X=O, NH, S, CO or $CH_2$ are generally described in the literature (for X=O: D. M. B. Hickey et al., J. Chem. Soc. Perkin Trans. I, 3097-3102, 1988; Z.-W. Guo et al., J. Org. Chem., 62, 6700-6701, 1997; D. M. T. Chan et al., Tetrahedron Lett., 39, 2933-2936, 1998; D. A. Evans et al., Tetrahedron Lett., 39, 2937-2940, 1998; G. M. Salamonczyk et al., Tetrahedron Lett., 38, 6965-6968, 1997; J.-F. Marcoux, J. Am. Chem. Soc., 119, 10539-10540, 1997; A. V. Kalinin et al., J. Org. Chem., 64, 2986-2987, 1999; for X=N: D. M. T. Chan et al., Tetrahedron Lett., 39, 2933-2936, 1998; J. P. Wolfe et al., J. Am. Chem. Soc., 118, 7215, 1996; M. S. Driver, J. F. Hartwig, J. Am. Chem. Soc., 118, 7217, 1996; see references in the review by C. G. Frost, P. Mendonca, J. Chem. Soc. Perkin I, 2615-2623, 1998; for X=S: C. R. Harringtcn, Biochem. J., 43, 434-437, 1948; A. Dibbo et al., J. Chem. Soc., 2890-2902, 1961; N. Yokoyama et al., U.S. Pat. No. 5,401,772, 1995; for X=CO or $CH_2$: L. Horner, H. H. G. Medem, Chem. Ber., 85, 520-530, 1952; G. Chiellini et al., Chemistry & Biology, 5, 299-306, 1998).

Scheme 4

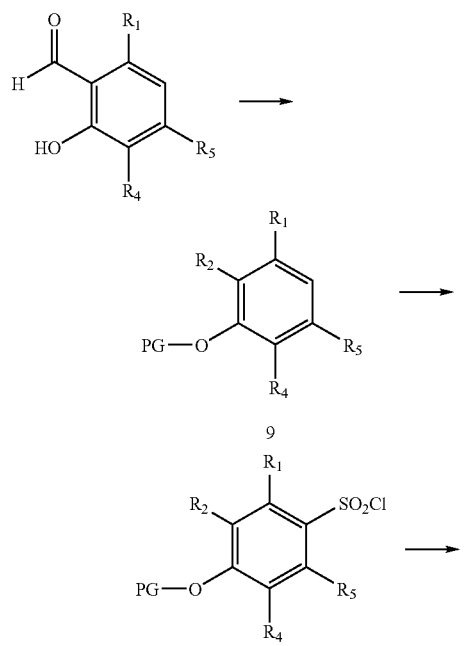

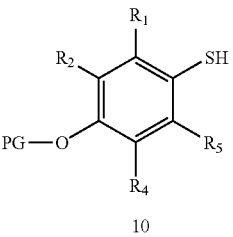

Compounds of formula I where X is S, SO or $SO_2$ can be prepared as outlined in Scheme 4. Beginning with the appropriate phenolic ether 9, chlorosulfonolation with chlorosulfonic acid in a solvent such as $CH_2Cl_2$ followed by reduction with a metal such Zn in aq. $H_2SO_4$ or AcOH generates the aryl thiol 10. Thiol 10 can be coupled with aryl halides of structure 5, then reduced, acylated and deprotected to generate compounds of Formula I where X is S. Compounds of Formula I where X is SO or $SO_2$ can be prepared in a similar manner except that prior to deprotection the sulfur is oxidized to the appropriate oxidation state using m-chloroperbenzoic acid. Phenolic ether 9 are either commercially available or in the case where $R_2$ is iPr readily prepared following the procedure of R. M. Jones et al, J. Org. Chem., 2001, 66, 3435-3441 by sequential treatment of the appropriate substituted salicylaldehyde with BOC anhydride and excess alkyl lithium.

Scheme 5

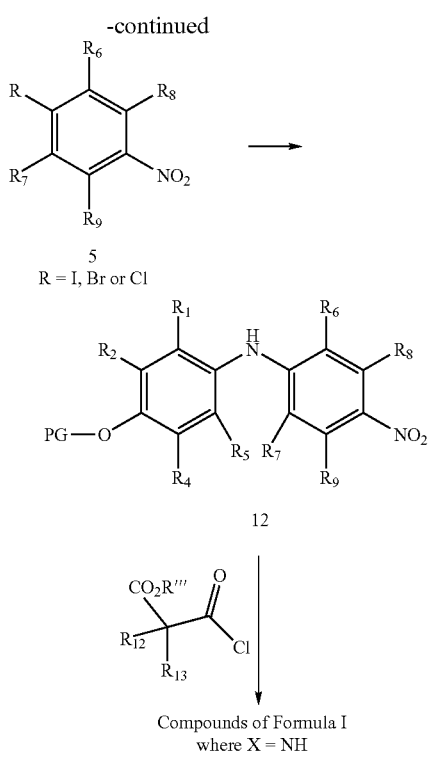

In a similar fashion (Scheme 5) compounds of Formula I where X is NH can be prepared by nitration of 9, reduction to the aniline 11 followed by coupling with 5 to generate the desired diaryl amine 12. Anilines represented by 12 can be converted to compounds of Formula I where X is NH following reduction, acylation and deprotection.

converted to compounds of formula I where X is CO following Fe mediated reduction of the $NO_2$ group, acylation and deprotection. Subsequent reduction of the ketone carbonyl with $Et_3SiH/BF_3.Et_2O$ generates compounds of formula I where X is $CH_2$.

Utilities & Combinations

A. Utilities

The compounds of the present invention are thyroid receptor ligands, and include compounds which are, for example, selective agonists, partial agonists, antagonists or partial antagonists of the thyroid receptor. Preferably compounds of the present invention possess activity as agonists of the thyroid receptor, and may be used in the treatment of diseases or disorders associated with thyroid receptor activity. In particular, compounds of the present invention may be used in the treatment of diseases or disorders associated with metabolic dysfunction or which are dependent upon the expression of a $T_3$ regulated gene.

Accordingly, the compounds of the present invention can be administered to mammals, preferably humans, for the treatment of a variety of conditions and disorders, including, but not limited to hypothyroidism; subclinical hyperthyroidism; non-toxic goiter; atherosclerosis; thyroid hormone replacement therapy (e.g., in the elderly); malignant tumor cells containing the thyroid receptor; papillary or follicular cancer; maintenance of muscle strength and function (e.g., in the elderly); reversal or prevention of frailty or age-related functional decline ("ARFD") in the elderly (e.g., sarcopenia); treatment of catabolic side effects of glucocorticoids; prevention and/or treatment of reduced bone mass, density or growth (e.g., osteoporosis and osteopenia); treatment of chronic fatigue syndrome (CFS); accelerating healing of complicated fractures, e.g. distraction osteogenesis; in joint replacement; eating disorders (e.g., anorexia); treatment of obesity and growth retardation associated with obesity; treatment of depression, nervousness, irritability and stress;

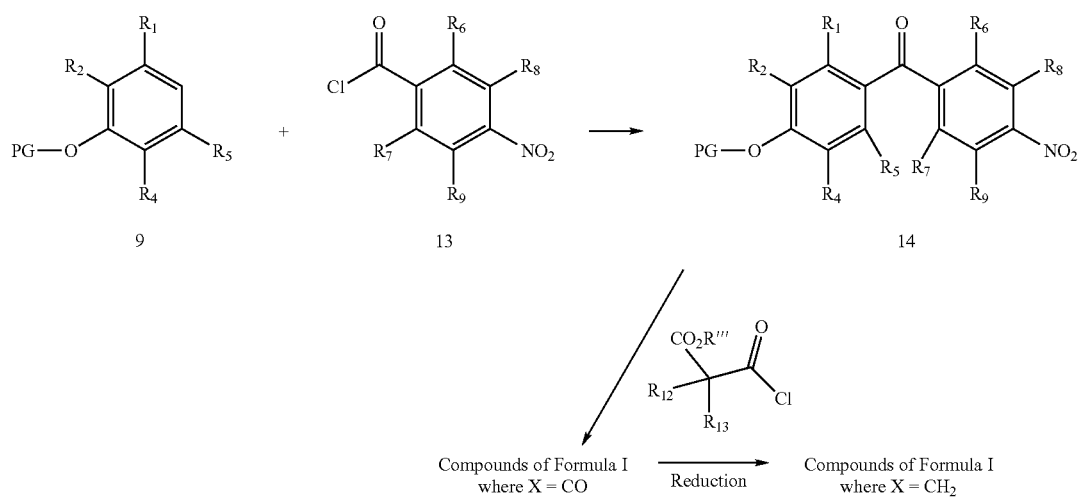

Scheme 6

Compounds of formula I where X is CO or $CH_2$ (Scheme 6) can be prepared by acylation of compound 9 with an acid chloride such as 13 in the presence of a Lewis acid catalyst such $AlCl_3$ in a solvent such as $CS_2$ or $CH_2Cl_2$ to generate the prerequisite ketone 14. Ketones represented by 14 can be treatment of reduced mental energy and low self-esteem (e.g., motivation/assertiveness); improvement of cognitive function (e.g., the treatment of dementia, including Alzheimer's disease and short term memory loss); treatment of catabolism in connection with pulmonary dysfunction and ventilator dependency; treatment of cardiac dysfunction (e.g., associated with valvular disease, myocardial infarction, cardiac hypertrophy or congestive heart failure); lowering blood pressure; protection against ventricular dysfunction or prevention of reperfusion events; treatment of hyperinsulinemia; stimulation of osteoblasts, bone remodeling and cartilage growth; regulation of food intake; treatment of insulin resistance, including NIDDM, in mammals (e.g., humans); treatment of insulin resistance in the heart; treatment of congestive heart failure; treatment of musculoskeletal impairment (e.g., in the elderly); improvement of the overall pulmonary function; skin disorders or diseases, such as glucocorticoid induced dermal atrophy, including restoration of dermal atrophy induced by topical glucocorticoids, and the prevention of dermal atrophy induced by topical glucocorticoids (such as the simultaneous treatment with topical glucocorticoid or a pharmacological product including both glucocorticoid and a compound of the invention), the restoration/prevention of dermal atrophy induced by systemic treatment with glucocorticoids, restoration/prevention of atrophy in the respiratory system induced by local treatment with glucocorticoids, UV-induced dermal atrophy, dermal atrophy induced by aging (wrinkles, etc.), wound healing, keloids, stria, cellulite, roughened skin, actinic skin damage, lichen planus, ichtyosis, acne, psoriasis, Dernier's disease, eczema, atopic dermatitis, chloracne, pityriasis and skin scarring.

The term treatment is also intended to include prophylactic treatment.

In addition, the conditions, diseases, and maladies collectively referenced to as "Syndrome X" or Metabolic Syndrome as detailed in Johannsson *J. Clin. Endocrinol. Metab.*, 82, 727-34 (1997), may be treated employing the compounds of the invention.

B. Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other compounds of the invention, or in combination with one or more other therapeutic agent(s), e.g., an antidiabetic agent or other pharmaceutically active material.

The compounds of the present invention may be employed in combination with other modulators and/or ligands of the thyroid receptor or other suitable therapeutic agents useful in the treatment of the aforementioned disorders including: anti-diabetic agents; anti-osteoporosis agents; anti-obesity agents; growth promoting agents (including growth hormone secretagogues); anti-inflammatory agents; anti-anxiety agents; anti-depressants; anti-hypertensive agents; cardiac glycosides; cholesterol/lipid lowering agents; appetite suppressants; bone resorption inhibitors; thyroid mimetics (including other thyroid receptor agonists); anabolic agents; and anti-tumor agents.

Examples of suitable anti-diabetic agents for use in combination with the compounds of the present invention include biguanides (e.g., metformin or phenformin), glucosidase inhibitors (e.g, acarbose or miglitol), insulins (including insulin secretagogues or insulin sensitizers), meglitinides (e.g., repaglinide), sulfonylureas (e.g., glimepiride, glyburide, gliclazide, chlorpropamide and glipizide), biguanide/glyburide combinations (e.g., Glucovance®), thiazolidinediones (e.g., troglitazone, rosiglitazone and pioglitazone), PPAR-alpha agonists, PPAR-gamma agonists, PPAR alpha/gamma dual agonists, SGLT2 inhibitors, glycogen phosphorylase inhibitors, inhibitors of fatty acid binding protein (aP2), glucagon-like peptide-1 (GLP-1), and dipeptidyl peptidase IV (DP4) inhibitors.

Examples of suitable anti-osteoporosis agents for use in combination with the compounds of the present invention include alendronate, risedronate, PTH, PTH fragment, raloxifene, calcitonin, RANK ligand antagonists, calcium sensing receptor antagonists, TRAP inhibitors, selective estrogen receptor modulators (SERM) and AP-1 inhibitors.

Examples of suitable anti-obesity agents for use in combination with the compounds of the present invention include aP2 inhibitors, PPAR gamma antagonists, PPAR delta agonists, beta 3 adrenergic agonists, such as AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, a lipase inhibitor, such as orlistat or ATL-962 (Alizyme), a serotonin (and dopamine) reuptake inhibitor, such as sibutramine, topiramate (Johnson & Johnson) or axokine (Regeneron), other thyroid receptor beta drugs, such as a thyroid receptor ligand as disclosed in WO 97/21993 (U. Cal SF), WO 99/00353 (KaroBio) and GB98/284425 (KaroBio), a cannabinoid-1 receptor antagonist, such as SR-141716 (Sanofi) and/or an anorectic agent, such as dexamphetamine, phentermine, phenylpropanolamine or mazindol.

The compounds of the present invention may be combined with growth promoting agents, such as, but not limited to, TRH, diethylstilbesterol, theophylline, enkephalins, E series prostaglandins, compounds disclosed in U.S. Pat. No. 3,239,345, e.g., zeranol, and compounds disclosed in U.S. Pat. No. 4,036,979, e.g., sulbenox or peptides disclosed in U.S. Pat. No. 4,411,890.

The compounds of the invention may also be used in combination with growth hormone secretagogues such as GHRP-6, GHRP-1 (as described in U.S. Pat. No. 4,411,890 and publications WO 89/07110 and WO 89/07111), GHRP-2 (as described in WO 93/04081), NN703 (Novo Nordisk), LY444711 (Lilly), MK-677 (Merck), CP424391 (Pfizer) and B-HT920, or with growth hormone releasing factor and its analogs or growth hormone and its analogs or somatomedins including IGF-1 and IGF-2, or with alpha-adrenergic agonists, such as clonidine or serotinin 5-$HT_D$ agonists, such as sumatriptan, or agents which inhibit somatostatin or its release, such as physostigmine and pyridostigmine. A still further use of the disclosed compounds of the invention is in combination with parathyroid hormone, PTH(1-34) or bisphosphonates, such as MK-217 (alendronate).

A still further use of the compounds of the invention is in combination with estrogen, testosterone, a selective estrogen receptor modulator, such as tamoxifen or raloxifene, or other androgen receptor modulators, such as those disclosed in Edwards, J. P. et al., *Bio. Med. Chem. Let.*, 9, 1003-1008 (1999) and Hamann, L. G. et al., *J. Med. Chem.*, 42, 210-212 (1999).

A further use of the compounds of this invention is in combination with steriodal or non-steroidal progesterone receptor agonists ("PRA"), such as levonorgestrel, medroxyprogesterone acetate (MPA).

Examples of suitable anti-inflammatory agents for use in combination with the compounds of the present invention include prednisone, dexamethasone, Enbrel®, cyclooxygenase inhibitors (i.e., COX-1 and/or COX-2 inhibitors such as NSAIDs, aspirin, indomethacin, ibuprofen, piroxicam, Naproxen®, Celebrex®, Vioxx®), CTLA4-Ig agonists/antagonists, CD40 ligand antagonists, IMPDH inhibitors, such as mycophenolate (CellCept®), integrin antagonists, alpha-4 beta-7 integrin antagonists, cell adhesion inhibitors, interferon gamma antagonists, ICAM-1, tumor necrosis factor (TNF) antagonists (e.g., infliximab, OR1384), prostaglandin synthesis inhibitors, budesonide, clofazimine, CNI-1493, CD4 antagonists (e.g., priliximab), p38 mitogen-activated protein kinase inhibitors, protein tyrosine kinase (PTK) inhibitors, IKK inhibitors, and therapies for the treatment of irritable bowel syndrome (e.g., Zelmac® and Maxi-K® openers such as those disclosed in U.S. Pat. No. 6,184,231 B1).

Example of suitable anti-anxiety agents for use in combination with the compounds of the present invention include diazepam, lorazepam, buspirone, oxazepam, and hydroxyzine pamoate.

Examples of suitable anti-depressants for use in combination with the compounds of the present invention include citalopram, fluoxetine, nefazodone, sertraline, and paroxetine.

For the treatment of skin disorders or diseases as described above, the compounds of the present invention may be used alone or optionally in combination with a retinoid, such as tretinoin, or a vitamin D analog.

Examples of suitable anti-hypertensive agents for use in combination with the compounds of the present invention include beta adrenergic blockers, calcium channel blockers (L-type and T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Examples of suitable cardiac glycosides for use in combination with the compounds of the present invention include digitalis and ouabain.

Examples of suitable cholesterol/lipid lowering agents for use in combination with the compounds of the present invention include HMG-CoA reductase inhibitors, squalene synthetase inhibitors, fibrates, bile acid sequestrants, ACAT inhibitors, MTP inhibitors, lipooxygenase inhibitors, an ileal Na+/bile acid cotransporter inhibitor, cholesterol absorption inhibitors, and cholesterol ester transfer protein inhibitors (e.g., CP-529414).

MTP inhibitors which may be employed herein in combination with one or more compounds of formula I include MTP inhibitors as disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885,983 and U.S. Pat. No. 5,962,440 all incorporated herein by reference.

The HMG CoA reductase inhibitors which may be employed in combination with one or more compounds of formula I include mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Further HMG CoA reductase inhibitors which may be employed herein include fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, pyrazole analogs of mevalonolactone derivatives as disclosed in U.S. Pat. No. 4,613,610, indene analogs of mevalonolactone derivatives, as disclosed in PCT application WO 86/03488, 6-[2-(substituted-pyrrol-1-yl)-alkyl)pyran-2-ones and derivatives thereof, as disclosed in U.S. Pat. No. 4,647,576, Searle's SC-45355 (a 3-substituted pentanedioic acid derivative) dichloroacetate, imidazole analogs of mevalonolactone, as disclosed in PCT application WO 86/07054, 3-carboxy-2-hydroxy-propane-phosphonic acid derivatives, as disclosed in French Patent No. 2,596,393, 2,3-disubstituted pyrrole, furan and thiophene derivatives, as disclosed in European Patent Application No. 0221025, naphthyl analogs of mevalonolactone, as disclosed in U.S. Pat. No. 4,686,237, octahydronaphthalenes, such as disclosed in U.S. Pat. No. 4,499,289, keto analogs of mevinolin (lovastatin), as disclosed in European Patent Application No. 0,142,146 A2, as well as other known HMG CoA reductase inhibitors.

The squalene synthetase inhibitors which may be used in combination with the compounds of the present invention include, but are not limited to, α-phosphono-sulfonates disclosed in U.S. Pat. No. 5,712,396, those disclosed by Biller et al, J. Med. Chem., 1988, Vol. 31, No. 10, pp 1869-1871, including isoprenoid (phosphinylmethyl)phosphonates, terpenoid pyrophosphates disclosed by P. Ortiz de Montellano et al, J. Med. Chem., 1977, 20, 243-249, the farnesyl diphosphate analog A and presqualene pyrophosphate (PSQ-PP) analogs as disclosed by Corey and Volante, J. Am. Chem. Soc., 1976, 98, 1291-1293, phosphinylphosphonates reported by McClard, R. W. et al, J.A.C.S., 1987, 109, 5544 and cyclopropanes reported by Capson, T. L., PhD dissertation, June, 1987, Dept. Med. Chem. U of Utah, Abstract, Table of Contents, pp 16, 17, 40-43, 48-51, as well as other squalene synthetase inhibitors as disclosed in U.S. Pat. Nos. 4,871,721 and 4,924,024 and in Biller, S. A., Neuenschwander, K., Ponpipom, M. M., and Poulter, C. D., Current Pharmaceutical Design, 2, 1-40 (1996).

Bile acid sequestrants which may be used in combination with the compounds of the present invention include cholestyramine, colestipol and DEAE-Sephadex (Secholex®, Policexide®), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid, acipimox, acifran, neomycin, p-aminosalicylic acid, aspirin, poly(diallylmethylamine) derivatives such as disclosed in U.S. Pat. No. 4,759,923, quaternary amine poly(diallyldimethylammonium chloride) and ionenes such as disclosed in U.S. Pat. No. 4,027,009, and other known serum cholesterol lowering agents.

ACAT inhibitors suitable for use in combination with compounds of the invention include ACAT inhibitors as described in, Drugs of the Future 24, 9-15 (1999), (Avasimibe); "The ACAT inhibitor, Cl-1011 is effective in the prevention and regression of aortic fatty streak area in hamsters", Nicolosi et al, Atherosclerosis (Shannon, Irel). (1998), 137(1), 77-85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16-30; "RP 73163: a bioavailable alkylsulfinyl-diphenylimidazole ACAT inhibitor", Smith, C., et al, Bioorg. Med. Chem. Lett. (1996), 6(1), 47-50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173-98, Publisher: CRC, Boca Raton, Fla.; "ACAT inhibitors: potential anti-atherosclerotic agents", Sliskovic et al, Curr. Med. Chem. (1994), 1(3), 204-25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359-62.

Examples of suitable cholesterol absorption inhibitor for use in combination with the compounds of the invention include SCH48461 (Schering-Plough), as well as those disclosed in Atherosclerosis 115, 45-63 (1995) and J. Med. Chem. 41, 973 (1998).

Examples of suitable ileal Na$^+$/bile acid cotransporter inhibitors for use in combination with the compounds of the invention include compounds as disclosed in Drugs of the Future, 24, 425-430 (1999).

Examples of suitable thyroid mimetics for use in combination with the compounds of the present invention include thyrotropin, polythyroid, KB-130015, and dronedarone.

Examples of suitable anabolic agents for use in combination with the compounds of the present invention include testosterone, TRH diethylstilbesterol, estrogens, β-agonists, theophylline, anabolic steroids, dehydroepiandrosterone, enkephalins, E-series prostagladins, retinoic acid and compounds as disclosed in U.S. Pat. No. 3,239,345, e.g., Zeranol®; U.S. Pat. No. 4,036,979, e.g., Sulbenox® or peptides as disclosed in U.S. Pat. No. 4,411,890.

The aforementioned patents and patent applications are incorporated herein by reference.

The above other therapeutic agents, when employed in combination with the compounds of the present invention, may be used, for example, in those amounts indicated in the Physicians' Desk Reference (PDR) or as otherwise determined by one of ordinary skill in the art.

Where the compounds of the invention are utilized in combination with one or more other therapeutic agent(s), either concurrently or sequentially, the following combination ratios and dosage ranges are preferred:

When combined with a hypolypidemic agent, an antidepressant, a bone resorption inhibitor and/or an appetite suppressant, the compounds of formula I may be employed in a weight ratio to the additional agent within the range from about 500:1 to about 0.005:1, preferably from about 300:1 to about 0.01:1.

Where the antidiabetic agent is a biguanide, the compounds of formula I may be employed in a weight ratio to biguanide within the range from about 0.01:1 to about 100:1, preferably from about 0.5:1 to about 2:1.

The compounds of formula I may be employed in a weight ratio to a glucosidase inhibitor within the range from about 0.01:1 to about 100:1, preferably from about 0.5:1 to about 50:1.

The compounds of formula I may be employed in a weight ratio to a sulfonylurea in the range from about 0.01:1 to about 100:1, preferably from about 0.2:1 to about 10:1.

The compounds of formula I may be employed in a weight ratio to a thiazolidinedione in an amount within the range from about 0.01:1 to about 100:1, preferably from about 0.5:1 to about 5:1.

The thiazolidinedione may be employed in amounts within the range from about 0.01 to about 2000 mg/day, which may optionally be administered in single or divided doses of one to four times per day.

Further, where the sulfonylurea and thiazolidinedione are to be administered orally in an amount of less than about 150 mg, these additional agents may be incorporated into a combined single tablet with a therapeutically effective amount of the compounds of formula I.

Metformin, or salt thereof, may be employed with the compounds of formula I in amounts within the range from about 500 to about 2000 mg per day, which may be administered in single or divided doses one to four times daily.

The compounds of formula I may be employed in a weight ratio to a PPAR-alpha agonist, a PPAR-gamma agonist, a PPAR-alpha/gamma dual agonist, an SGLT2 inhibitor and/or an aP2 inhibitor within the range from about 0.01:1 to about 100:1, preferably from about 0.5:1 to about 5:1.

An MTP inhibitor may be administered orally with the compounds of formula I in an amount within the range of from about 0.01 mg/kg to about 100 mg/kg and preferably from about 0.1 mg/kg to about 75 mg/kg, one to four times daily.

A preferred oral dosage form, such as tablets or capsules, may contain the MTP inhibitor in an amount of from about 1 to about 500 mg, preferably from about 2 to about 400 mg, and more preferably from about 5 to about 250 mg, administered on a regimen of one to four times daily.

For parenteral administration, the MTP inhibitor may be employed in an amount within the range of from about 0.005 mg/kg to about 10 mg/kg and preferably from about 0.005 mg/kg to about 8 mg/kg, administered on a regimen of one to four times daily.

A HMG CoA reductase inhibitor may be administered orally with the compounds of formula I within the range of from about 1 to 2000 mg, and preferably from about 4 to about 200 mg.

A preferred oral dosage form, such as tablets or capsules, will contain the HMG CoA reductase inhibitor in an amount from about 0.1 to about 100 mg, preferably from about 5 to about 80 mg, and more preferably from about 10 to about 40 mg.

A squalene synthetase inhibitor may be administered with the compounds of formula I within the range of from about 10 mg to about 2000 mg and preferably from about 25 mg to about 200 mg.

A preferred oral dosage form, such as tablets or capsules, will contain the squalene synthetase inhibitor in an amount of from about 10 to about 500 mg, preferably from about 25 to about 200 mg.

The compounds of formula I of the invention can be administered orally or parenterally, such as subcutaneously or intravenously, as well as by nasal application, rectally or sublingually to various mammalian species known to be subject to such maladies, e.g., humans, in an effective amount within the dosage range of abut 0.01 μg/kg to about 1000 μg/kg, preferably about 0.1 μg/kg to 100 μg/kg, more preferably about 0.2 μg/kg to about 50 μg/kg (or from about 0.5 to 2500 mg, preferably from about 1 to 2000 mg) in a regimen of single, two or four divided daily doses.

The compounds of the formula I can be administered for any of the uses described herein by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compounds of formula I can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Exemplary compositions for nasal aerosol or inhalation administration include solutions in saline which can contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for rectal administration include suppositories which can contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition.

The following working examples serve to better illustrate, but not limit, some of the preferred embodiments of the present invention.

EXAMPLE 1

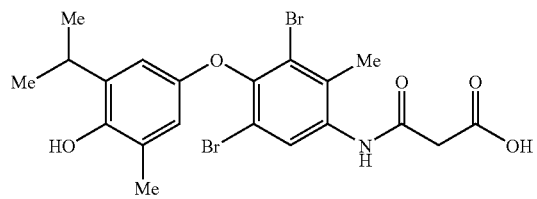

3-[N-[3,5-dibromo-4-[4-hydroxy-3-(1-methylethyl-5-methyl)-phenoxy]-2-methylphenyl]amino]-3-oxo-propanoic acid

1A.

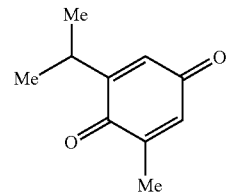

Following the procedure of N. Jacobsen, *J.C.S. Perkin Trans.* 1979, 2, 569, 30% aq. H$_2$O$_2$ (2.6 mL, 23.3 mmol) was added to a stirred solution of 3-isopropyl-5-methyl phenol (1 g, 6.6 mmol) in a 2.5:1 TFA/THF at a rate to maintain 20° C. After 18 hr the brown orange solution was diluted with Et$_2$O and quenched by addition of solid NaHCO$_3$. The violet organic layer was washed repeatedly with 5% K$_2$CO$_3$ until the violet color no longer remained, whereupon, the solution was dried over Na$_2$SO$_4$. After removal of the volatiles, 0.48 g of a yellow oil was obtained. The crude 2-isopropyl-6-methylquinone was used directly since it was prone to degrade to form two more polar compounds.

1B.

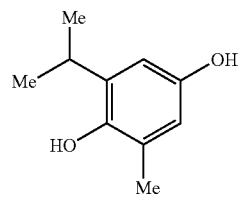

To a stirred solution of 2-isopropyl-6-methylquinone (68 mg, 0.4 mmol) in 75% aq EtOH (4 mL) was added N$_2$S$_2$O$_4$ (72 mg, 0.4 mmol). Heating for 1 hr at 60° C. produced ~50% conversion; Subsequent addition of an additional equiv of $Na_2S_2O_4$ and heating for a $2^{nd}$ hr converted the remaining quinone to product. After dilution with aq. $NH_4Cl$, the reaction was extracted 3× with EtOAc. The combined EtOAc layers were washed with brine prior to drying over $Na_2SO_4$. The residue, after removal of the volatiles under vacuum, were chromatographed on silica gel using 15% EtOAc/hexane to elute 45 mg of desired 2-isopropyl-6-methylhydroquinone as a white solid.

1C.

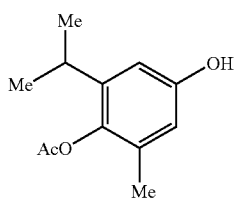

To a stirred 4 solution of 2-isopropyl-6-methylhydroquinone (50 mg, 0.3 mmol) and DMAP (4 mg, 0.1 mmol) in pyridine (1 mL)was added AcCl (55 μL, 2.5 mmol). After slowly warming to 20, the reaction was stirred for 4 hr prior to quenching with 1N HCl and extracting 3× with EtOAc. The residue, obtained after the combined EtOAc layers were dried over $Na_2SO_4$ and concentrated, was chromatographed on silica gel using 20% EtOAc/hexane to elute 69 mg of desired bis acetylated hydroquinone. The desired mono 4-acetate was generated by slowly adding a solution of NaOH (12 mg, 0.29 mmol) and $Na_2S_2O_4$ (13 mg, 0.75 mmol) in $H_2O$ (0.1 mL) to the above bis acetate (0.28 mmol)in EtOH (1 mL). After 30 min, the reaction was quenched by addition of 1N HCl followed by removal of EtOH under vacuum. The residue, after dissolution in EtOAc, was washed with $NH_4Cl$ followed by brine prior to drying over $Na_2SO_4$. After removal of the volatiles chromatography on silica gel with 15% EtOAc/hexane eluted 45 mg of desired 3-isopropyl-5-methyl-4-acetoxyphenol.

1D.

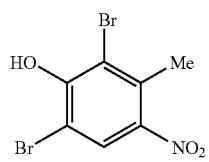

To 3-methyl-4-nitrophenol (1 g, 6.5 mmol) dissolved in 1:1 $MeOH/CH_2Cl_2$ solution (40 mL) at 0C was added $BnNMe_3^+ Br_3^-$ (2.55, 6.5 mmol) and $CaCO_3$ (0.65 g, 6.5 mmol) The reaction, being deemed complete after 40 min by HPLC analysis, was quenched by addition of 1N HCl (30 mL). After the MeOH and $CH_2Cl_2$ were removed under vacuum, the solids were collected by filtration and washed with $H_2O$ to yield 2,6-dibromo-3-methyl-4-nitrophenol as a white solid (2 g, 99%).

1E.

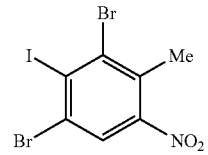

To a stirred solution of 2,6-dibromo-3-methyl-4-nitrophenol (2 g, 6.43 mmol) in $CH_2Cl_2$ (20 mL) at 0° C. was added $Et_3N$ (1.34 mL, 9.5 mmol) followed by dropwise addition of $Tf_2O$ (1.2 mL, 7 mmol). After warming to 20° C. and stirring 2 hr, the reaction was quenched with $H_2O$. The organic layer was washed 1× with $H_2O$ and brine before drying over $MgSO_4$. Without further purification, the resulting black oil, obtained after removal of the volatiles under vacuum, along with NaI (2 g, 13 mmol) was heated at 100° C. in DMF (15 mL) for 16 hr. Upon cooling, the reaction was diluted with $Et_2O$, washed 2× with $H_2O$ and once with brine. After drying over $MgSO_4$, the residue, obtained after removal of the volatiles under vacuum, was chromatographed on silica gel using 2-5% EtOAc/hexane as an eluent to yield 1.38 g of 3,5-dibromo-4-iodo-2-methylnitrobenzene (50%) as an off-white solid.

1F.

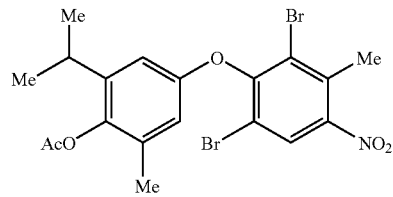

A stirred mixture of $K_2CO_3$ (242 mg, 1.75 mmol), 3-isopropyl-5-methyl-4-acetoxyphenol (670 mg, 1.59 mmol) prepared in Part 1B and 3,5-dibromo-4-iodo-2-methylnitrobenzene (670 mg, 1.59 mmol) prepared in Part 1E in DMF (33 mL) was heated for 18 hr at 70° C. whereupon HPLC analysis revealed both components to have been consumed. After dilution with $Et_2O$ and sat'd aq. $NH_4Cl$, the mixture was extracted 2× with $Et_2O$. The combined layers were washed with $NH_4Cl$ followed by brine prior to drying over $MgSO_4$. After removal of the volatiles, chromatography on silica gel with 10-25% EtOAc/hexane eluted 370 mg of desired diaryl ether as a yellow solid.

1G.

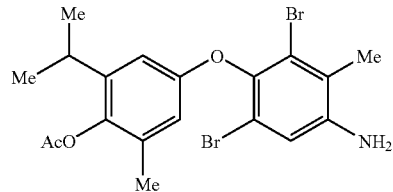

To a stirred solution of nitro diaryl ether prepared in Part 1F (369 mg, 0.74 mmol) in a 1:9 $H_2O/AcOH$ (14.6 mL) was added Fe powder (206 mg, 3.69 mmol). After stirring for 3 hr at 20° C., HPLC analysis revealed that the starting material was consumed. Once the AcOH was removed under vacuum, the residue was diluted with EtOAc (75 mL) and H₂O (50 mL)₃ and extracted 2× with EtOAc. The combined EtOAc layers, after being washed with brine and drying over Na₂SO₄, were concentrated to yield 352 mg of product as a off-white foam that was used without further purification. 1H.

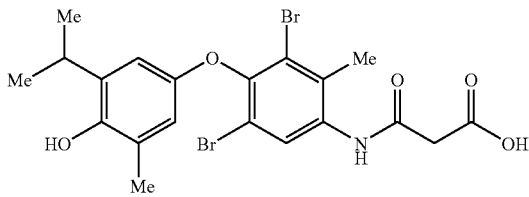

To a stirred solution of the 4-aminodiaryl ether of Part 1G (353 mg, 0.748 mmol) in THF (15 mL) was added ethyl malonyl chloride (169 mg, 1.12 mmol) and Et₃N (189 mg, 1.87 mmol). After 20 hr at 20° C., the reaction was quenched by addition of sat'd aq. NH₄Cl and the THF removed under vacuum. After dissolution of the residue in EtOAc, the solution was washed sequentially twice with aq. NH₄Cl before drying over Mg₂SO₄. Removal of the volatiles yielded 438 mg of a yellow foam that was converted to the final product by stirring for 19 hr at 40° C. in 4:1 THF/H₂O (25 mL) containing LiOH.H₂O (157 mg, 3.74 mmol). After removal of the THF under vacuum, the pH of the reaction was adjusted to pH 1 with 1N HCl prior to 2 EtOAc extractions. The combined layers were washed with aq. NH₄Cl, dried over MgSO₄ and concentrated. The resulting orange reside (385 mg) was dissolved in MeCN prior to purification by preparative HPLC employing aq. MeCN containing 0.1% TFA as eluent to yield 225 mg of desired final product as a white foam.

1H NMR (400 MHz, acetone-d6) δ 9.35 (s, 1H), 8.027 (s, 1H), 6.47 (d, J=3.1 Hz, 1H), 6.22 (d, J=3 Hz, 1H), 3.49 (s, 2H), 3.22 (septet, J=7 Hz, 1H), 2.32 (s, 3H), 2.07 (s, 3H), 1.05 (d, J=7.0 Hz, 6H). HPLC: LUNA 4.6×50 mm, 0 to 100% B over 4 min, 8 ml/min, 3 min hold time, A=10% methanol/water+0.2% H₃PO₄, B=90% methanol/water+ 0.2% H₃PO₄, retention time=7.43 min. LCMS found 511.8, 513.7, 515.7 (M−H)⁻.

EXAMPLE 2

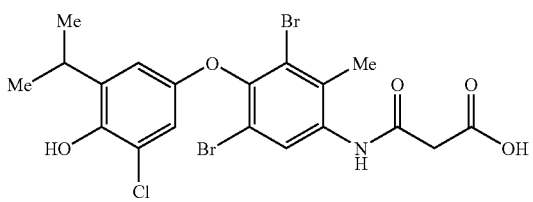

3-[N-[3,5-dibromo-4-[4-hydroxy-3-(1-methylethyl-5-chloro)-phenoxy]-2-methylphenyl]amino]-3-oxo-propanoic acid

2A.

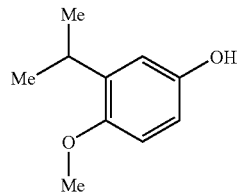

To a stirred 20° C. solution comprised of KOH (1154 g, 4.75 mol), Bu₄N⁺ HSO₄⁻ (140 g, 0.41 mol) in H₂O (5.6 L) was added commercially available 2-isopropylphenol (590 g, 4.33 mol) in CH₂Cl₂ (5.6 L). After 30 min, MeI (741 g, 5.22 mol) was added prior to stirring the reaction overnight. After separation of the layers, Et₃N (185 mL, 1.3 mol) was added to the CH₂Cl₂ fraction to destroy the residual MeI. After 15 min, the CH₂Cl₂ was removed under vacuum and the salts suspended in cyclohexane (4 L) prior to filtration. The cyclohexane filtrate was sequentially washed with 2N HCl followed by 2 brine washes. Concentration under vacuum yielded 2-isopropylanisole (612 g, 94%) as a light yellow oil.

To a stirred solution of 2-isopropylanisole (859 g, 5.85 mol) and POCl₃ (2690 g, 17.5 mol) at 80° C. under N₂, was slowly added DMF (1584 mL, 20.46 mol) at a rate such that the temperature remained between 80-90° C. After stirring for 16 hr at 85° C., the dark solution was poured cautiously onto 7 Kg of ice. (Quench required 1.5 hr due to violent exotherm) The mixture was extracted twice with EtOAc (total volume 16 L). The combined EtOAc layers were washed once with aq. NaHCO₃ and then with brine. Upon concentration, 881 g of 4-formyl-2-isopropylanisole was obtained.

To a solution of 4-formyl-2-isopropylanisole (880 g, 4.94 mol) in THF (4.56 L) and cyclohexane (3.74 L) at 20° C. was added a solution of NaHSO₃ (1.31 kg, 12.56 mol) in H₂O (4.36 L). After stirring overnight, the crystals were collected by filtration, washed with 3:1 cyclohexane/THF prior to drying under vacuum to yield 1.3 kg of bisulfite adduct. To a stirred solution of the dried adduct in 1:4 H₂O/MeOH (13 L) containing p-TosOH H₂O (908 g, 4.77 mol), 30% H₂O₂ (1.625 L, 16.1 mol) was slowly added over 1.75 hr at a rate such that the temperature remained between 0-5° C. After stirring overnight at 20° C., the reaction was monitored by HPLC. Additional H₂O₂ was added if starting material remained. Upon completion, the reaction was cooled to 4° C., whereupon a solution of Na₂SO₃ (1.86 kg, 10.68 mo) in 6.5 L of H₂O was added at a rate such that the temperature did not exceed 34° C. After stirring for 1 hr, the solids were filtered and washed with EtOAc. The aqueous layer was extracted with EtOAc. The combined EtOAc fractions were washed sequentially with aq. NaHCO₃ and brine. Upon concentration, 3-isopropyl-4-methoxyphenol (510 g, 67% conversion) was obtained in 93% purity.

2B.

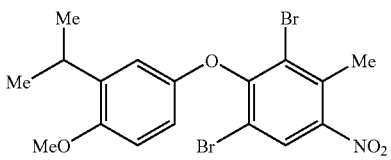

A stirred mixture of K$_2$CO$_3$ (224 mg, 1.6 mmol), 3-isopropyl-4-methoxyphenol (224 mg, 1.34 mmol, prepared in Part 2A) and 3,5-dibromo-4-iodo-2-methylnitrobenzene (567 mg, 1.34 mmol prepared in Example 1 Part E) in DMF (10 mL) was heated for 48 hr at 75° C. whereupon HPLC analysis revealed the reaction was complete. After dilution with Et$_2$O and sat'd aq. NH$_4$Cl, the mixture was extracted 2× with Et$_2$O. The combined layers were washed with NH$_4$Cl 3× followed by brine prior to drying over MgSO$_4$. After removal of the volatiles, chromatography on silica gel with 2-5% EtOAc/hexane eluted 320 mg of desired diaryl ether as a yellow solid.

2C.

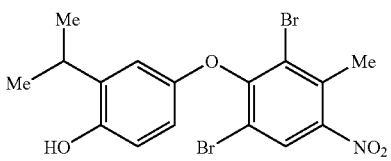

To a stirred 0° C. CH$_2$Cl$_2$ solution (7 mL) containing the methoxydiaryl ether (320 mg, 0.7 mmol) prepared in Part 2B was added BBr$_3$ (72 µL, 0.77 mmol). After stirring for 16 hr at 0° C., the reaction, being complete by TLC analysis, was quenched with H$_2$O. Following removal of the CH$_2$Cl$_2$, the residue was dissolved in EtOAc. The EtOAc layer, after being washed 2× with sat'd aq NH$_4$Cl, was dried over MgSO$_4$. The residue obtained after concentration under vacuum was chromatographed on silica gel using 15-30% EtOAc/hexane to elute 264 mg of phenolic diaryl ether.

2D.

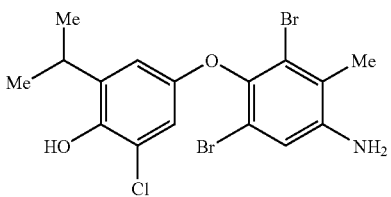

To a stirred 20° C. HOAc solution (5 mL) containing the phenolic diaryl ether of Part 2C (264 mg, 0.59 mmol) was added BnNMe$_3^+$ ICL$_4^-$ (250 mg, 0.59 mmol). After 1 hr, the solids were filtered, whereupon H$_2$O (1 mL) and Fe dust (165 mg, 3 mmol) were added to the filtrate. The reaction was stirred for 16 hr at 40° C. After removal of HOAc under vacuum, the reaction was diluted with EtOAc (50 mL) and aq. NaHCO$_3$ (50 mL). The slurry was then filtered prior to two EtOAc extractions. The combined EtOAc fractions were subsequently washed 2× with aq NaHCO$_3$, 1× with brine followed by drying over MgSO$_4$. After concentration under vacuum the residue was chromatographed on silica gel using 10-20% EtOAc/hexane as eluant to obtain 210 mg of desired diaryl ether.

2E.

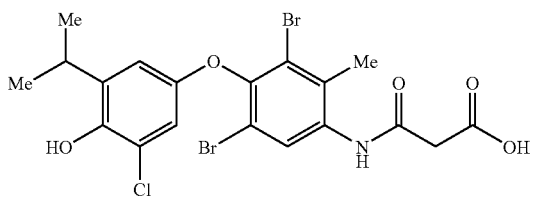

To a stirred 0° C. solution of the 4-aminodiaryl ether of Part 2D (210 mg, 0.47 mmol) in 10:1 THF/H$_2$O (5.5 mL) was added NaHCO$_3$ (194 mg, 2.35 mmol) followed by ethyl malonyl chloride (66 µL, 0.52 mmol). After warming to 20° C. over 1 hr, and stirring an additional hour, the reaction was quenched by addition of sat'd aq. NH$_4$Cl. Following removal of the THF under vacuum, the residue, after dissolution in EtOAc, was washed sequentially twice with aq. NH$_4$CL before drying over Mg$_2$SO$_4$. The crude product was purified by chromatography on silica gel using 20% EtOAc/hexane to elute the desired half ester half amide which was converted to the final product by stirring for 4 hr at 20° C. in 4:1 THF/H$_2$O (5 mL) containing LiOH.H$_2$O (60 mg, 1.5 mmol). After removal of the THF under vacuum, the pH of the reaction was adjusted to pH 2 with 1N HCl. The resulting white solid was collected by filtration and air-dried to yield 160 mg of desired final product.

1H NMR (400 MHz, d6-acetone) δ 9.50 (s, 1H), 8.17 (s, 1H), 6.77 (d, J=3.1 Hz, 1H), 6.49 (d, J=3.1 Hz, 1H), 3.58 (s, 2H), 3.33 (m, 1H), 2.44 (s, 3H), 1.17 (d, J=7.0 Hz, 6H). 13C NMR (400 MHz, d6-acetone) δ 170.08, 165.20, 150.84, 147.00, 145.40, 139.37, 136.07, 133.50, 128.53, 122.00, 121.38, 115.00, 113.46, 112.98, 42.42, 28.20, 22.59, 18.50. HPLC: LUNA 4.6×50 mm, 0 to 100% B over 4 min, 4 ml/min, 1 min hold time, A=10% methanol/water+10 mm NH4OAc, B=90% methanol/water+10 mm NH4OAc, retention time=3.40 min. LCMS found 534.00 (M+H)+. HRMS found 533.9330 (C19H19Br2ClNO5, (M+H)+). CHN Analysis found C 41.00%, H 3.50%, N 2.47%.

EXAMPLE 3

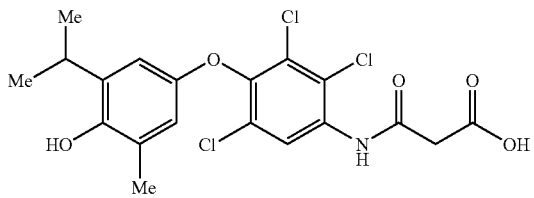

3-[N-[2,3,5-trichloro-4-[4-hydroxy-3-(1-methyl-ethyl-5-methyl)-phenoxy]phenyl]amino]-3-oxopropanoic acid

3A.

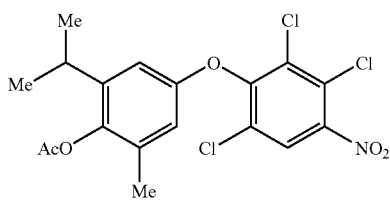

A mixture of 2,3,4,5-tetrachloronitrobenzene (400 mg, 1.53 mmol), 3-isopropyl-5-methyl-4-acetoxyphenol (319 mg, 1.53 mmol), prepared as described in part C Example 1, and K$_2$CO$_3$ (254 mg, 1.84 mmol) in DMF (3.8 mL) was stirred vigorously for 23 hr at 20° C. The reaction was diluted with EtOAc (200 mL) prior to washing the organic layer 3× with a total 500 mL of 1N HCl, 1× brine and drying over MgSO$_4$. Concentration under vacuum yielded a yellow oil which was chromatographed on silica gel using hexane as eluent to obtain 448 mg of desired diaryl ether.
3B.

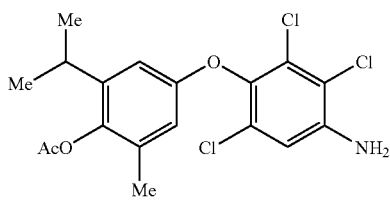

A mixture of the nitrodiaryl ether of Part 3A (435 mg, 1 mmol) and Fe powder (112 mg, 2 mmol) in HOAc (5 mL) was stirred at 20° C. for 48 hr until complete by HPLC analysis. The reaction was diluted with EtOAc and H$_2$O (100 mL each). Upon phase separation, the organic layer was washed with 100 mL portions of H$_2$O 1× and aq NaHCO$_3$ 2× prior to drying over MgSO$_4$. Concentration under vacuum yielded yellow oil which was chromatographed on silica gel using hexane—5% EtOAc/hexane as eluant to obtain 355 mg of desired diaryl ether.
3C.

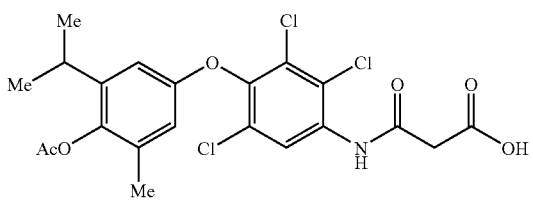

To a stirred solution of the 4-aminodiaryl ether of Part 3B (355 mg, 0.88 mmol) in CH$_2$Cl$_2$ (4.4 mL) was added ethyl malonyl chloride (146 mg, 0.97 mmol), pyridine (214 μL, 2.6 mmol) and DMAP (10 mg, 0.09 mmol). After 20 hr at 20° C., the reaction was cooled to 0° C. prior to addition of 3 mL of 1N HCl. After stirring for 10 min, an additional 30 mL of CH$_2$Cl$_2$ and 1N HCl were added. Upon phase separation, the organic layer was washed with 1N HCl. Following concentration under vacuum, chromatography on silica gel using hexane—5% EtOAc/hexane as eluant yielded 115 mg of desired acylated diaryl ether as a yellow foam.
3D.

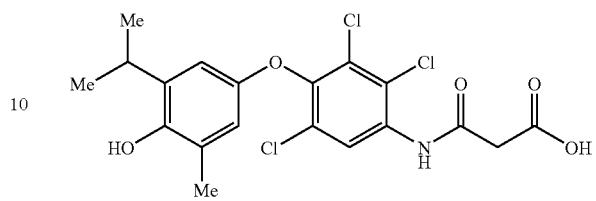

A solution of the ethyl ester of Part 3C (115 mg, 0.22 mmol) and LiOH.H$_2$O (19 mg, 0.45 mmol) in 1:2:3 H2O/THF/MeCN (1.1 mL) was stirred overnight. After addition of 1 mL of 1N HCl, the mixture was purified by reverse phase preparative HPLC employing aq. MeCN containing 0.1% TFA as eluant to yield 16 mg of desired final product as a white foam.

1H NMR (CD3CN, 400 MHz) δ 9.47 (s, 1H), 8.38 (s, 1H), 6.56 (d, 1H, J=3.1 Hz), 6.32 (d, 1H, J=3.1 Hz), 3.51 (s, 2H), 3.17 (septet, 1H, J=6.8 Hz), 1.10 (d, 6H, J=6.9 Hz) 13C NMR (CD3CN, 100 MHz) δ 169.22, 164.89, 149.92, 146.83, 136.46, 133.34, 128.84, 127.50, 125.54, 121.29, 113.16, 110.04, 40.83, 26.65, 21.63, 15.64. HPLC: 2.59 min, 96.4% HI. Column: YMS S-5 C18 4.6×50 mm. Gradient: 0-100% B over 4 min. Solvent A: 10% CH3CN/H2O+0.1% TFA. Solvent B: 90% CH3CN/H2O+0.1% TFA. Flow rate: 4 mL/min. Monochrome detection at 220 nm.

Low Res MS: Anal. Calc'd for C19H18Cl3NO5: 445. found: m/z 445. High Res. MS Anal. Calc'd for C19H18Cl3NO5 445.02506 found: m/z 444.0175 [M−H].

EXAMPLE 4

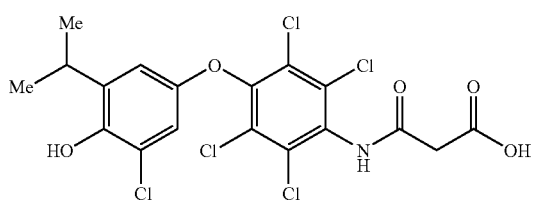

3-[N-[2,3,5,6-tetrachloro-4-[4-hydroxy-3-(1-methyl-ethyl-5-chloro)-phenoxy]phenyl]amino]-3-oxopropanoic acid

4A.

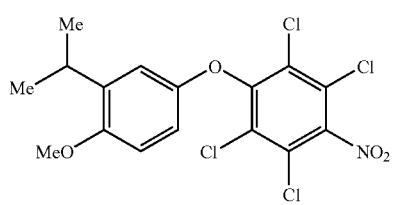

A mixture of 2,3,4,5,6-pentachloronitrobenzene (897 mg, 3.0 mmol), 3-isopropyl-4-methoxyphenol (505 mg, 3.0 mmol), prepared in part A Example 2, and K$_2$CO$_3$ (503 mg, 1.6 mmol) in DMF (15 mL) was stirred vigorously for 23 hr at 20° C. The reaction was diluted with EtOAc (150 mL) prior to washing the organic layer 2× with a total 150 mL of 1N HCl, 1× brine and drying over MgSO$_4$. Concentration under vacuum yielded 1.3 g of a red oil which was chromatographed on silica gel using 15% EtOAc/hexane as eluant to obtain 644 mg of desired diaryl ether as yellow oil. 4B.

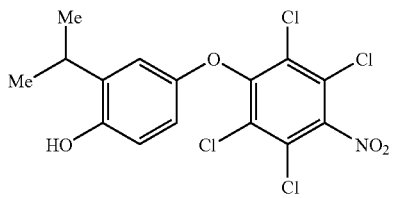

To a stirred −78° C. CH$_2$Cl$_2$ solution (1 mL) containing the methoxydiaryl ether (644 mg, 1.5 mmol) prepared in Part 4A was added 1M BBr$_3$ in CH$_2$Cl$_2$ (15 mL, 15 mmol). The reaction, after warming slowly to 20° C., was stirred for 18 hr whereupon it was quenched by cautious addition to ice-cold H$_2$O (100 mL). After extracting the mixture twice with CH$_2$Cl$_2$, the combined CH$_2$Cl$_2$ layers were washed with brine prior to drying over MgSO$_4$. The residue, obtained after concentration under vacuum, was chromatographed on silica gel using 15-40% EtOAc/hexane to elute 415 mg of phenolic diaryl ether as a yellow oil. 4D.

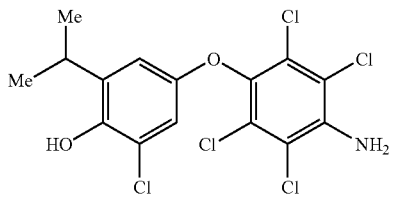

To a stirred 20° C. HOAc solution (8 mL) containing the phenolic diaryl ether of Part 4C (660 mg, 1.61 mmol) was added BnNMe$_3^+$ ICl$_4^-$ (675 mg, 1.61 mmol). After 1 hr, the solids were filtered, whereupon Fe dust (450 mg, 8 mmol) was added to the filtrate. The reaction was stirred for 3 days at 20° C. After removal of HOAc under vacuum, the reaction was diluted with H$_2$O (50 mL) before extracting 3× with EtOAc. The combined organic layers were washed sequentially with aq NaHCO$_3$ and brine prior to drying over MgSO$_4$. After concentration under vacuum the residue was chromatographed on silica gel using 10-25% EtOAc/hexane as eluent to obtain 540 mg of desired diaryl ether. 4E.

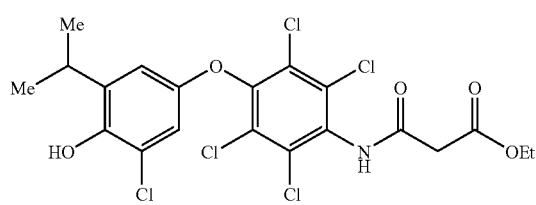

To a stirred 0° C. solution of the 4-aminodiaryl ether of Part 4D (350 mg, 0.84 mmol) in CH$_2$Cl$_2$ (4 mL) was added ethyl malonyl chloride (126 mg, 0.84 mmol) and pyridine (200 μL, 2.5 mmol. After 1.5 hr at 0° C., the reaction was quenched by addition of 3 mL of 1N HCl. After stirring for 10 min, an additional 30 mL of CH$_2$Cl$_2$ and 1N HCl were added. Upon phase separation, the organic layer was washed with 1N HCl. Following concentration under vacuum, chromatography on silica gel using 15-30% EtOAc/hexane as eluant yielded 120 mg of desired acylated diaryl ether. 4F.

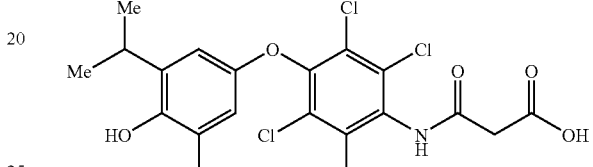

A solution of the ethyl ester of Part 4E (115 mg, 0.22 mmol) and LiOH.H$_2$O (28 mg, 0.66 mmol) in 1:2:3 H$_2$O/THF/MeCN (1 mL) was stirred overnight. After addition of 1 mL of 1N HCl, the mixture was purified by reverse phase preparative HPLC employing aq. MeCN containing 0.1% TFA as eluent to yield 53 mg of desired final product as a white foam.

1H NMR (CD3CN, 400 MHz) δ 8.96 (s, 1H), 6.91 (d, 1H, J=3.0 Hz), 6.73 (d, 1H, J=3.0 Hz), 6.61 (br s, 1H), 3.65 (s, 2H), 3.37 (septet, 1H, J=6.8 Hz), 1.28 (d, 6H, J=6.9 Hz) HPLC: 2.6 min, 96.4% HI. Column: YMS S-5 C18 4.6×50 mm. Gradient: 0-100% B over 4 min. Solvent A: 10% CH3CN/H2O+0.1% TFA. Solvent B: 90% CH3CN/H2O+ 0.1% TFA. Flow rate: 4 mL/min. Monochrome detection at 220 nm. LC-MS: [M+H] 499.88, 501.87, 503.88, 505.88 Low Res MS: Anal. Calc'd for C18H14Cl5NO5: 498. found: m/z 499 [M+H]. High Res. MS Anal. Calc'd for C18H14Cl5NO5: 498.93146 found: m/z 499.9391 [M+H].

EXAMPLE 5

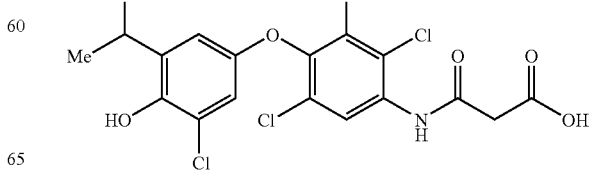

3-[N-[2,3,5-trichloro-4-[4-hydroxy-3-(1-methyl-ethyl-5-chloro)-phenoxy]phenyl]amino]-3-oxopropanoic acid

5A.

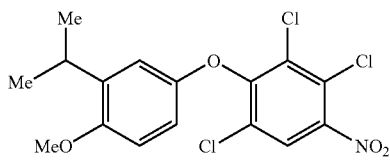

A mixture of 2,3,4,5-tetrachloronitrobenzene (707 mg, 2.7 mmol), 3-isopropyl-4-methoxyphenol (450 mg, 2.7 mmol), prepared in Example 2 Part A, and $K_2CO_3$ (449 mg, 3.25 mmol) in DMF (9 mL) was stirred vigorously at 20° C. for 60 hr. The reaction was diluted with EtOAc (150 mL) prior to washing the organic layer 2× with a total 150 mL of 1N HCl, 1× with $H_2O$ then brine and drying over $MgSO_4$. Concentration under vacuum yielded 1.73 g of a red oil which was chromatographed on silica gel using 5% EtOAc/hexane as an eluant to obtain 810 mg of desired diaryl ether.

5B.

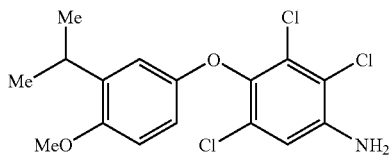

To a solution of the nitrodiarylether of Part 5A (800 mg, 2.05 mmol) in HOAc (20 mL) was added Fe dust (343 mg, 6.15 mmol). After stirring for 20 hr at 20° C., the HOAc was removed under vacuum. The residue was diluted with $H_2O$ (30 mL) before extracting 3× with EtOAc. The combined organic layers were washed sequentially with aq $NaHCO_3$ and brine prior to drying over $MgSO_4$. After concentration under vacuum the residue was chromatographed on silica gel using hexane—25% EtOAc/hexane as eluant to obtain 540 mg of desired diaryl ether as a white solid.

5C.

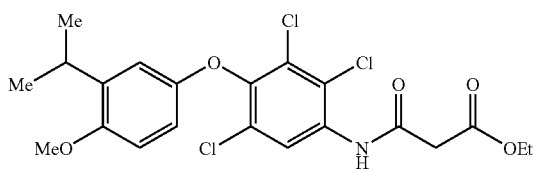

To a stirred solution of the 4-aminodiaryl ether of Part 5B (540 mg, 1.5 mmol) in THF (30 mL) was added ethyl malonyl chloride (339 mg, 2.25 mmol), $Et_3N$ (379 mg, 3.7 mmol). After 1 hr at 20° C., the reaction was quenched with sat'd aq $NH_4Cl$. Removal of the THF under vacuum was followed by partitioning the residue between EtOAc and sat'd aq. $NH_4CL$. The EtOAc layer was washed sequentially with sat'd aq. $NH_4CL$ and brine before drying over $Mg_2SO_4$. Following concentration under vacuum, the residue was chromatographed on silica gel using 10-30% EtOAc/hexane to elute 550 mg of desired acylated diaryl ether.

5D.

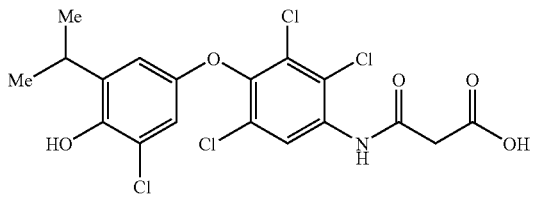

To a −78° C. solution of the 4-methoxydiaryl ether of Part 5C (550 mg, 1.6 mmol) in $CH_2Cl_2$ (12 mL) was added $BBr_3$ (2.9 g, 11.6 mmol). The reaction was stirred overnight at 20° C., whereupon it was quenched with $H_2O$ (20 mL). After extraction of the mixture 3× with EtOAc, the combined EtOAc fractions were washed with brine before drying over $MgSO_4$. Following concentration under vacuum, the residue was dissolved in 2:1 THF/$H_2O$ (18 mL) along with $LiOH.H_2O$ (122 mg, 2.9 mmol). The resulting solution was stirred for 16 hr, then concentrated under vacuum and diluted with EtOAc and $H_2O$. The pH was adjusted to 1-2 with 1N HCl before extracting 3× with EtOAc. The combined EtOAc fractions were washed with brine and dried over $MgSO_4$ before concentration under vacuum to obtain 513 mg of product. To a −25° C. MeCN solution (20 mL) containing a portion of the crude product (200 mg, <0.46 mmol) was added t-BuOCl (50 mg, 0.46 mmol). When after 1 hr at −20° C. HPLC analysis revealed the reaction to be incomplete, a second portion of t-BuOCl (26 mg, 0.24 mmol) was added. After 3 hr, upon increasing the temperature to −5, side products began to form. The reaction was cooled to −10° C., quenched with aq $NaHSO_3$ and concentrated. Following dilution with aq. $NH_4Cl$, the mixture was extracted 3× with EtOAc. The combined EtOAc fractions were washed with brine and dried over $MgSO_4$ before concentration under vacuum. The crude product was purified by reverse phase prep chromatography using aq MeCN containing 0.1% TFA to elute 6.5 mg of the desired final product.

1H NMR (CD3CN, 400 MHz) δ 9.56 (s, 1H) 8.45 (s, 1H), 6.74 (d, 1H, J=3.1 Hz), 6.59 (d, 1H, J=3.0 Hz), 6.43 (br s, 1H), 3.52 (s, 2H), 3.24 (septet, 1H, J=6.9 Hz), 1.14 (d, 6H, J=6.9 Hz) HPLC: 2.78 min, 99.1% HI. Column: YMS S-5 C18 4.6×50 mm. Gradient: 0-100% B over 4 min. Solvent A: 10% CH3CN/H2O+0.1% TFA. Solvent B: 90% CH3CN/H2O+0.1% TFA. Flow rate: 4 mL/min. Monochrome detection at 220 nm. LC-MS: [M+H] 466.09, 468.09, 470.09 [M−H] 464.02, 466.02

Low Res MS: Anal. Calc'd for C18H15Cl4NO5: 464.97. found: m/z 465 [M+H]. High Res. MS Anal. Calc'd for C18H15Cl4NO5 m/z 464.97043 found: m/z 463.9639 [M−H].

EXAMPLE 6

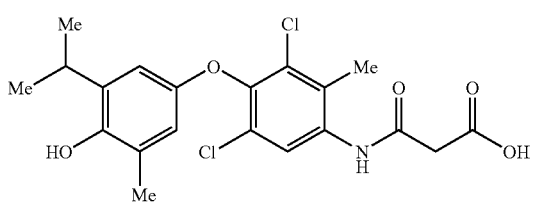

3-[N-[3,5-dichloro-4-[4-hydroxy-3-(1-methylethyl-5-methyl)-phenoxy]-2-methylphenyl]amino]-3-oxo-propanoic acid

6A.

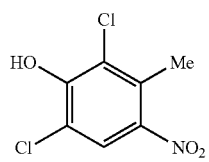

A solution of 3-methyl-4-nitrophenol (1.74 g, 11.36 mmol) and BnNMe$_3^+$ ICl$_4^-$ (9.52, 22.7 mmol) in ACOH (235 mL) was heated with stirring at 70° C. for 18 hr. After cooling, the newly precipitated orange solid was removed by filtration; and the filter cake washed with AcOH. The combined filtrates were concentrated under vacuum whereupon the residue was partitioned between EtOAc/H$_2$O. After separation of phases, the EtOAc layer was washed with brine, dried over MgSO$_4$, and concentrated to yield 3.06 g of a brown solid. Chromatography on silica gel eluting with hexane—5% EtOAc/hexane yielded 1.71 g (70%) of 2,6-dichloro-3-methyl-4-nitrophenol as a yellow orange solid.

6B.

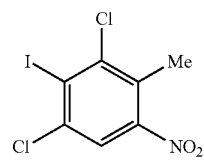

To a stirred solution of 2,6-dichloro-3-methyl-4-nitrophenol (1.71 g, 7.7 mmol) in CH$_2$Cl$_2$ (10 mL) at -10° C. was added Et$_3$N (1.09 g, 10.8 mmol) followed by dropwise addition of Tf$_2$O (2.39 g, 8.4 mmol). After warming to 20° C. and stirring 3 days, the reaction was quenched with H$_2$O. The combined fractions of two CH$_2$Cl$_2$ extracts were washed 1× sequentially with 1N HCl, aq. NaHCO$_3$ and brine before drying over MgSO$_4$. Without further purification, the resulting red brown oil (2.5 g) obtained after removal of the volatiles under vacuum, was heated with NaI (4.24 g, 28 mmol) while stirring at 100° C. in DMF (8 mL) for 18 hr. Upon cooling, the reaction was poured into ice/H$_2$O and stirred for 2 hr at 0° C. before filtration. The filter cake was washed with H$_2$O prior to drying under vacuum to yield 1.64 g of 3,5-dichloro-4-iodo-2-methylnitrobenzene (70%) as an off-white solid.

6C.

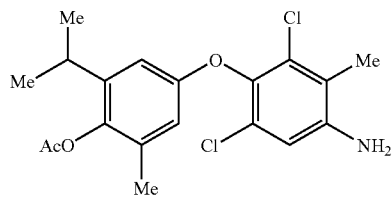

A stirred mixture of K$_2$CO$_3$ (344 mg, 2.5 mmol), 3-isopropyl-5-methyl-4-acetoxyphenol (471 mg, 2.26 mmol) prepared in Part C Example 1 and 3,5-dichloro-4-iodo-2-methylnitrobenzene (750 mg, 2.26 mmol) in DMF (47 mL) was heated for 19 hr at 70° C., whereupon HPLC analysis revealed both starting components to have been consumed. After dilution with EtAc (75 mL) and sat'd aq. NH$_4$Cl (95 mL), the mixture was extracted 2× with EtOAc. The combined layers were washed with twice with NH$_4$Cl prior to drying over MgSO$_4$. After removal of the volatiles, the residual brown oil (1.08 g) was dissolved in 1:8 H$_2$O/HOAc (52 mL). Following addition of Fe powder (730 mg, 13 mmol), the reaction was stirred 1.5 hr at 20° C. whereupon no starting nitrodiaryl remained by HPLC. Following removal of HOAc under vacuum, the residue was partitioned between EtOAc (130 mL) and H$_2$O (170 mL). After filtration of the resulting suspension through celite, the cake was washed with EtOAc. The phases of the filtrate were seperated and the aq layer extracted again with EtOAc. The combined EtOAc fractions were washed sequentially with sat'd aq NaHCO$_3$ and brine prior to drying over MgSO$_4$. Concentration under vacuum yielded a brown solid (0.9 g) that was chromatographed on silica gel with 20-30% EtOAc/hexane to elute 544 mg of the desired diaryl ether as an orange foam.

6D.

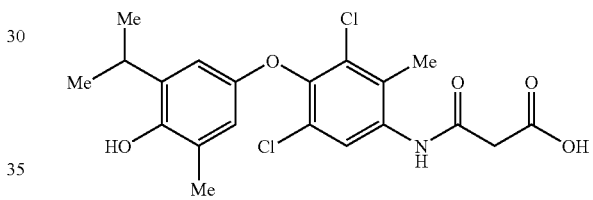

To a stirred solution of the 4-aminodiaryl ether of Part 6C (544 mg, 1.42 mmol) in THF (28.5 mL) was added ethyl malonyl chloride (322 mg, 2.14 mmol) and Et$_3$N (360 mg, 3.56 mmol). After 60 hr at 20° C., the reaction was quenched by addition of sat'd aq. NH$_4$Cl and the THF removed under vacuum. The residue after dissolution in EtOAc was washed sequentially twice with aq. NH$_4$Cl before drying over Mg$_2$SO$_4$. Removal of the volatiles yielded 749 mg of a orange foam which was converted to the final product by stirring for 19 hr in 4:1 THF/H$_2$O (50 mL) containing LiOH.H$_2$O (317 mg, 7.54 mmol) at 40° C. After removal of the THF under vacuum, the pH was adjusted to pH 1 with 1N HCl prior to 2 EtOAc extractions. The combined EtOAc layers were washed with aq. NH$_4$Cl, dried over MgSO$_4$ and concentrated. The resulting orange reside (656 mg) was dissolved in MeCN prior to purification by reverse phase preparative HPLC employing aq. MeCN containing 0.1% TFA as eluent to yield 356 mg of desired final product as a white foam.

1H NMR (400 MHz, acetone-d6) δ 9.49 (s, 1H), 8.0 (s, 1H), 6.634 (d, J=3 Hz, 1H), 6.37 (d, J=3 Hz, 1H), 3.62 (s, 2H), 3.35 (septet, J=7 Hz, 1H), 2.41 (s, 3H), 2.2 (s, 3H), 1.18 (d, J=7.0 Hz, 6H). HPLC: LUNA 4.6×50 mm, 0 to 100% B over 4 min, 4 ml/min, 1 min hold time, A=10% methanol/water+0.2% H$_3$PO$_4$, B=90% methanol/water+0.2% H$_3$PO$_4$, retention time=7.66 min. LRMS found 423.9, 425.8, 427.7 (M−H)$^−$.

EXAMPLE 7

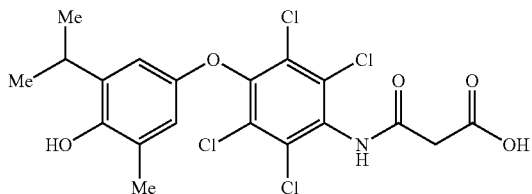

3-[N-[2,3,5,6-tetrachloro-4-[4-hydroxy-3-(1-methyl-ethyl-5-chloro)-phenoxy]phenyl]amino]-3-oxopropanoic acid

7A.

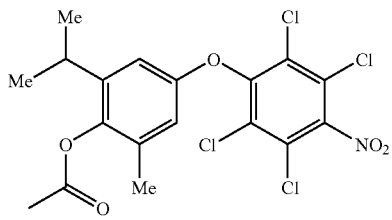

A mixture of 2,3,4,5,6-pentachloronitrobenzene (920 mg, 3.3 mmol), 3-isopropyl-5-methyl-4-acetoxyphenol (520 mg, 2.35 mmol), prepared as described in part C Example 1, and $K_2CO_3$ (576 mg, 4.2 mmol) in DMF (8 mL) was stirred vigorously for 72 hr at 20° C. The reaction was diluted with EtOAc (150 mL) prior to washing the organic layer 2× with a total 150 mL of 1N HCl, 1× brine and drying over $MgSO_4$. Concentration under vacuum yielded a dark oil that by LC/MS contained a ~2:1 mixture of two isomeric nitrated diaryl ethers. Chromatography on silica gel using 1:1 CH2Cl2/hexane as eluant effected partial enrichment; total yield was 800 mg. The major isomer (para nitro) eluted first.

7B.

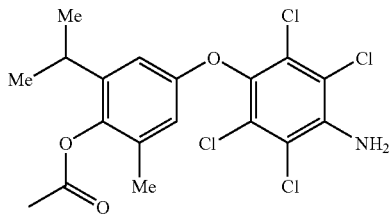

To a stirred 20° C. 9:1 HOAc/H2O solution (10 mL) containing the mixture of acetylated phenolic diaryl ethers of Part 7A (800 mg, 1.71 mmol) was added Fe dust (350 mg, 6.25 mmol). The reaction was stirred for 18 hr at 20° C., then heated to 50° C. for 3 hr to fully consume starting material. After removal of the volatiles under vacuum, the reaction was diluted with $H_2O$/EtOAc and filtered through celite. The filtrate was extracted 3× with EtOAc. The combined organic layers were washed sequentially with aq $NaHCO_3$ and brine prior to drying over $Na_2SO_4$. After concentration under vacuum the isomeric anilines were separated by preparative HPLC reverse phase chromatography using MeOH/$H_2O$ as eluent to obtain 320 mg of the desired para diaryl ether and 150 mg of the ortho isomer.

7C.

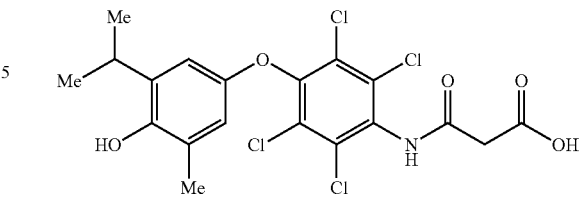

To a stirred 0° C. solution of the 4-aminodiaryl ether of Part 7B (130 mg, 0.3 mmol) in $CH_2Cl_2$ (1.5 mL) was added methyl malonyl chloride (44 mg, 0.33 mmol), DMAP (2 mg) and pyridine (50 μL, 0.6 mmol. After 4 hr at 0° C., the reaction was quenched by addition of 5 mL of 1N HCl.

After stirring for 10 min, an additional 30 mL of EtOAc and $H_2O$ were added prior to extracting 3× with EtOAc. The combined organic layers were washed with $H_2O$ and brine before drying over $Na_2SO_4$. Following concentration under vacuum, the crude residue (160 mg) was dissolved in 15 mL DMF. After addition of 5 mL of $H_2O$ containing 100 mg of KOH, the reaction was stirred for 18 hr. After removal of the volatiles under vacuum at 50° C., the residue was acidified with 1N aq HCl and extracted 3× with EtOAc. The combined organic layers were washed with $H_2O$ 2× and brine 1× before drying over $Na_2SO_4$. Following concentration under vacuum, the crude residue (160 mg) was purified by reverse phase preparative HPLC employing aq. MeCN containing 0.1% TFA as eluant to yield 56 mg of desired final product as a white foam.

1H NMR (400 MHz, d6-acetone) δ 9.63 (s, 1H), 6.70 (d, 1H, J=3.1 Hz), 6.40 (d, 1H, J=3.0 Hz), 3.61 (s, 2H), 3.33 (septet, 1H, J=6.8 Hz), 2.17 (s, 3H), 1.16 (d, 6H, J=6.9 Hz) HPLC: LUNA 4.6×50 mm, 0 to 100% B over 4 min, 4 ml/min, 1 min hold time, A=10% methanol/water+0.2% $H_3PO_4$, B=90% methanol/water+0.2% $H_3PO_4$, retention time 4.2 min. LC-MS: 481.9[M+H]$^+$; 479.9 (M–H)$^-$

EXAMPLE 8

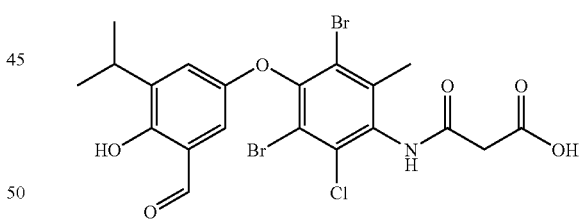

N-[3,5-Dibromo-4-[3-formyl-4-hydroxy-5-isopropylphenoxy]-2-methylphenyl]malonamic acid

8A.

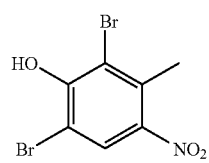

3-Methyl-4-nitrophenol (1.50 g, 9.75 mmol) was dissolved in a mixture of CH$_2$Cl$_2$ (30 mL) and methanol (30 mL) and cooled to 4° C. While stirring, benzyltrimethylammoniumtribromide (7.6 g, 19.5 mmol) and CaCO$_3$ (1.95 g, 19.5 mmol) was added and the reaction was allowed to warm to room temperature. After 30 minutes, 1N HCl (45 mL) was added and reaction mixture left for 16 hours at 4° C. The organic phase was removed in vacuo and the resulting precipitate was collected by filtration and washed by water. The damp solid was co-evaporated with toluene and Et$_2$O to yield 2.8 g (93%) of 2,6-dibromo-3-methyl-4-nitrophenol as a white solid.

8B.

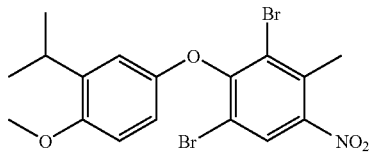

Bis-(3-isopropyl-4-methoxyphenyl)iodonium tetrafluoroborate of Part 8A (1.50 g, 2.93 mmol) and Copper powder (0.286 g, 4.50 mmol) was mixed in CH$_2$Cl$_2$ (10 mL) and the resulting suspension was cooled to 0° C. While stirring, a solution of 2,6-dibromo-3-methyl-4-nitrophenol (0.7 g, 2.25 mmol), Et$_3$N (0.63 mL, 4.5 mmol) and CH$_2$Cl$_2$ (5 mL) was added and the flask covered by aluminium foil. After 2 days stirring in the dark at room temperature the crude reaction mixture was washed with 1N HCl (15 mL) and a phase separator (IST) was used to separate the two phases. The aqueous phase was extracted by CHCl$_3$ and the collected organic phases were concentrated in vacuo. The crude residue was purified on column (MPLC, silica gel, gradient elution: n-heptane/EtOAc from 1:0 to 95:5) to give 561 mg (54%) of 4-(2,6-dibromo-3-methyl-4-nitrophenoxy)-2-isopropylanisole as a light yellow solid.

8C.

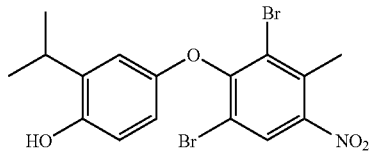

4-(2,6-Dibromo-3-methyl-4-nitrophenoxy)-2-isopropylanisole of Part 8B (560-mg, 1.22 mmol) was dissolved in CH$_2$Cl$_2$ (10 mL) and cooled to 0° C. Ice-cold BF$_3$-SMe$_2$ (5 mL, 47.5 mmol) was added and the temperature was allowed to reach room temperature. After 16 hours stirring at room temperature, the reaction mixture was quenched by ice water and stirred for 30 minutes. A phase separator (IST) was used to separate the two phases and the aqueous phase was extracted by CHCl$_3$. The collected organic phases were washed by brine and concentrated in vacuo. The residue was purified on column (MPLC, silica gel, gradient elution: n-heptane/EtOAc from 1:0 to 9:1) to give 250 mg (46%) of 4-(2,6-dibromo-3-methyl-4-nitrophenoxy)-2-isopropylphenol as light yellow syrup.

8D.

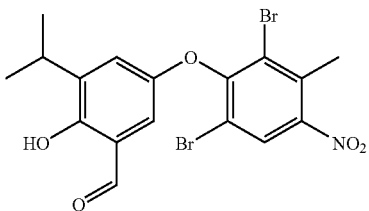

Hexamethylentetramine (197 mg, 1.4 mmol) was added to a solution of compound 4-(2,6-dibromo-3-methyl-4-nitrophenoxy)-2-isopropylphenol of Part 8C (250 mg, 0.56 mmol) and TFA (5 mL). The resulting reaction mixture was stirred for 16 hours at 95° C. The reaction mixture was cooled to room temperature and 1N HCl (10 mL) was added. After another hour of stirring, the reaction mixture was extracted with EtOAc (3×30 mL), the combined organic phases washed by 1N HCl (15 mL), H$_2$O (20 mL) and brine (20 mL). After drying over Na$_2$SO$_4$, concentration and filtration through a pad of silica, 210 mg (79%) of 5-(2,6-dibromo-3-methyl-4-nitrophenoxy)-2-hydroxy-3-isopropylbenzaldehyde was obtained as a light yellow solid.

8E.

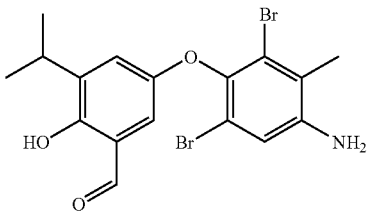

5-(2,6-Dibromo-3-methyl-4-nitrophenoxy)-2-hydroxy-3-isopropylbenzaldehyde of Part 8D (100 mg, 0.21 mmol), Na$_2$S$_2$O$_4$ (553 mg, 3.2 mmol), NaHCO$_3$ (0.2 mL, saturated aqueous solution) and ethanol (1.8 mL) were mixed in a microwave safe reaction vial. The vial was sealed and irradiated for 5 minutes at 140° C. NaHCO$_3$ (5 mL, saturated aqueous solution) was added to the reaction mixture and the organic phase removed in vacuo. The obtained suspension was extracted with CHCl$_3$ and the two phases were separated with phase separator (IST). The organic phase was concentrated and filtration through a pad of silica gave 25 mg (27%) of 5-(4-amino-2,6-dibromo-3-methylphenoxy)-2-hydroxy-3-isopropylbenzaldehyde as white foam.

8F.

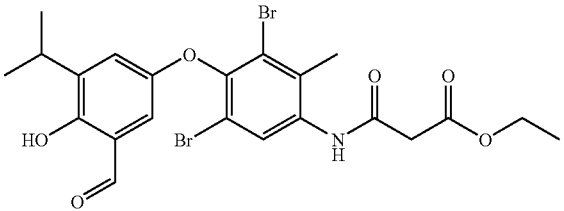

To a stirred solution of ethyl malonylchloride (7.2 µl, 0.056 mmol) and compound 5-(4-amino-2,6-dibromo-3-methylphenoxy)-2-hydroxy-3-isopropylbenzaldehyde of Part 8E (25 mg, 0.056 mmol) in THF (0.5 mL) was added Et$_3$N (15.7 µl, 0.112 mmol) at 4° C. After 30 minutes stirring at room temperature, the reaction mixture was washed with NH$_4$Cl (saturated aqueous solution) and the organic phase removed in vacuo. The water phase was extracted with CHC$_{13}$ and the two phases were separated with a phase separator (IST). The organic phase was concentrated and the resulting residue was purified on column (silica gel, gradient elution: n-heptane/EtOAc from 1:0 to 7:3) to give 15 mg (48%) of N-[3,5-dibromo-4-[3-formyl-4-hydroxy-5-isopropylphenoxy]-2-methylphenyl]-malonamic acid ethyl ester as a light yellow residue.

8G.

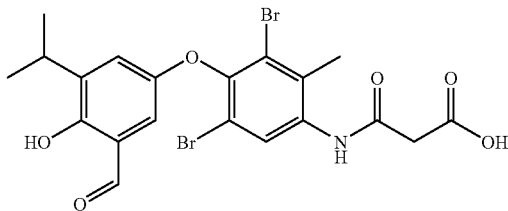

To a stirred solution of compound N-[3,5-dibromo-4-[3-formyl-4-hydroxy-5-isopropylphenoxy]-2-methyl-phenyl] malonamic acid ethyl ester of Part 8F (15 mg, 0.027 mmol) and THF (0.5 mL) was added LiOH (0.25 mL, 1N). After 1 hour of stirring the pH of reaction was adjusted to 1 with 1N HCl and the organic phase removed in vacuo. The residue was extracted with EtOAc (3×3 mL) and the combined organic phases were dried over $Na_2SO_4$ before concentration. The residue was purified on column (silica gel, gradient elution: $CHCl_3$/MeOH/AcOH from 1:0:0 to 90:10:1) to yield 6 mg (42%) of N-[3,5-dibromo-4-[3-formyl-4-hydroxy-5-isopropylphenoxy]-2-methylphenyl]malonamic acid as a white solid.

HPLC: YMC Pro C-8 reversed phase (2.1×50 mm),5 to 100% solvent B over 5 min, 1 ml/min, 3 min hold time, Solvent A=0.05% Formic acid in water, Solvent B=MeCN, retention time=4.38 min. LCMS found 526.2, 528.2, 530 $(M-H)^-$.

EXAMPLE 9

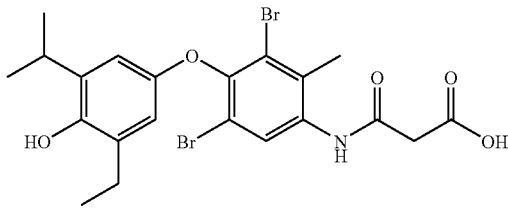

N-[3,5-dibromo-4-[3-ethyl-4-hydroxy-5-isopropylphenoxy]-2-methylphenyl]malonamic acid

9A.

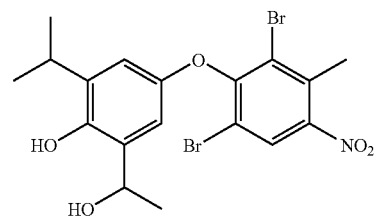

5-(2,6-Dibromo-3-methyl-4-nitrophenoxy)-2-hydroxy-3-isopropylbenzaldehyde of Part 8D (210 mg, 0.44 mmol) was dissolved in $CH_2Cl_2$ (5 mL) and cooled to 4° C. $Me_3Al$ in toluene (0.355 mL, 0.67 mmol, 2N) was added to the mixture and the reaction was stirred for 16 hours at room temperature. The reaction mixture was quenched with ice water and extracted with EtOAc. The organic phase was washed with water and brine, dried over $Na_2SO_4$ and concentrated in vacuo. Filtration through a pad of silica gave 195 mg (93%) of 4-(2,6-dibromo-3-methyl-4-nitrophenoxy)-2-(1-hydroxyethyl)-6-isopropylphenol as a light yellow solid.

9B.

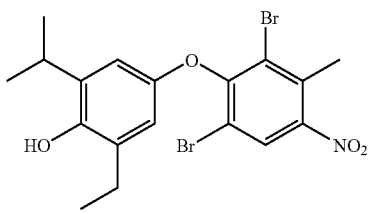

A solution of -(2,6-dibromo-3-methyl-4-nitrophenoxy)-2-(1-hydroxyethyl)-6-isopropylphenol of Part 9A (195 mg, 0.399 mmol) and TFA (4 mL) was treated with triethylsilane (0.255 mL, 1.59 mmol) and stirred for 1 hour at room temperature. The reaction mixture was concentrated and co-evaporated (toluene, $CH_2Cl_2$) to give a residue that was filtrated through a pad of silica. This gave 185 mg (98%) of 4-(2,6-dibromo-3-methyl-4-nitrophenoxy)-2-ethyl-6-isopropylphenol as a light yellow syrup.

9C.

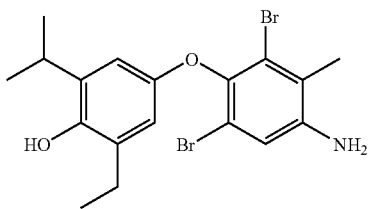

4-(2,6-dibromo-3-methyl-4-nitrophenoxy)-2-ethyl-6-isopropylphenol of Part 9B (165 mg, 0.344 mmol), $Na_2S_2O_4$ (910 mg, 5.23 mmol) and EtOH (3.2 mL) were mixed in a micro-wave safe reaction vial. The vial was sealed and irradiated for 10 minutes at 160° C. A saturated aqueous solution of $NaHCO_3$ (5 mL) was added to the reaction mixture and the organic phase concentrated in vacuo. The aqueous phase was extracted with EtOAc and the collected organic phases dried over $Na_2SO_4$. Concentration in vacuo gave a residue that was filtrated through a pad of silica. This gave 120 mg (79%) of 4-(4-amino-2,6-dibromo-3-methylphenoxy)-2-ethyl-6-isopropylphenol as a white foam.

9D.

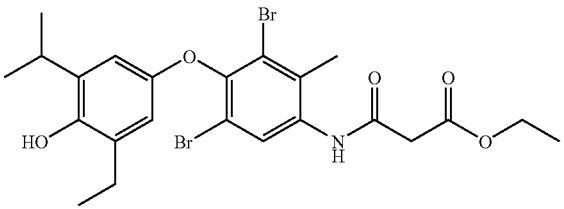

Ethylmalonylchloride (37 µl, 0.29 mmol) and $Et_3N$ (93 µl, 0.67 mmol) was added to a solution of 4-(4-amino-2,6- dibromo-3-methylphenoxy)-2-ethyl-6-isopropylphenol of Part 9C (120 mg, 0.27 mmol) in THF (3 mL). After 16 hours stirring at room temperature, the reaction mixture was quenched by NH₄Cl (saturated aqueous solution) and the organic phase removed in vacuo. The water phase was extracted with EtOAc and the organic phase was washed with NH₄Cl (2×3 mL, saturated aqueous solution). The organic phase was dried over Na₂SO₄, concentrated and filtrated through a pad of silica. This gave 130 mg (86%) of N-[3,5-dibromo-4-[3-ethyl-4-hydroxy-5-isopropylphenoxy]-2-methylphenyl]malonamic acid ethyl ester as a white foam.

9E.

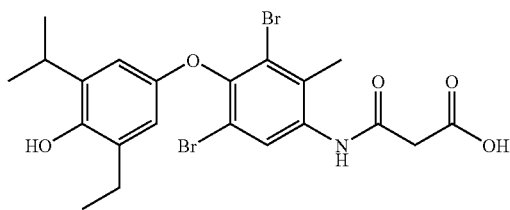

N-[3,5-dibromo-4-[3-ethyl-4-hydroxy-5-isopropylphenoxy]-2-methylphenyl]malonamic acid ethyl ester of Part 9D (130 mg, 0.23 mmol) was dissolved in THF (2 mL) and treated with LiOH (2 mL, 1N) for 1 hour at room temperature. The reaction was acidified with 1N HCl and concentrated in vacuo. The remaining water phase was extracted with EtOAc (3×5 mL) and the combined organic phases were dried over Na₂SO₄ before concentration in vacuo. The residue was purified on column (MPLC, silica gel, gradient elution: CHCl₃/MeOH/AcOH from 1:0:0 to 98:2:0.3) to give 50 mg (41%) of N-[3,5-dibromo-4-[3-ethyl-4-hydroxy-5-isopropylphenoxy]-2-methylphenyl]-malonamic acid as a white solid.

1H NMR (500 MHz, CD3OD) δ 8.0 (s, 1H), 6.39 (d, 1H), 6.2 (d, 1H), 3.4 (s, 2H), 3.2 (septet, 1H), 2.46 (q, 2H), 2.07 (s, 3H), 1.05 (d, 6H), 1.02 (t, 3H). HPLC: YMC Pro C-8 reversed phase (2.1×50 mm),5 to 100% solvent B over 5 min, 1 ml/min, 3 min hold time, Solvent A=0.05% Formic acid in water, Solvent B=MeCN, retention time=3.96 min. LCMS found 526.3, 528.2, 530 (M−H)⁻.

EXAMPLE 10

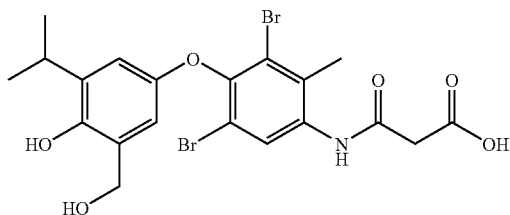

N-[3,5-dibromo-4-[4-hydroxy-3-hydroxymethyl-5-isopropylphenoxy]-2-methylphenyl]malonamic acid

10A.

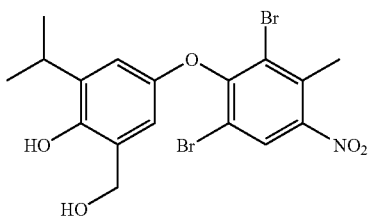

5-(2,6-Dibromo-3-methyl-4-nitrophenoxy)-2-hydroxy-3-isopropylbenzaldehyde of Part 8D (100 mg, 0.21 mmol) and NaBH₄ (9.0 mg, 0.23 mmol) was dissolved in a mixture of EtOH and THF (3 mL, 2:1) at room temperature. After 1.5 hours of stirring at room temperature, the reaction mixture was concentrated and the residue suspended in CHCl₃. The suspension was washed with 1N HCl and the two phases were separated with a phase separator (IST) before concentration of the organic phase. The residue was purified on column (silica gel, gradient elution: n-heptane/EtOAc from 1:0 to 7:3) to give 85 mg (85%) of 4-(2,6-dibromo-3-methyl-4-nitrophenoxy)-2-hydroxymethyl-6-isopropylphenol as a light yellow foam.

10B.

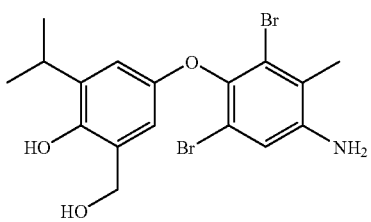

A mixture of compound 4-(2,6-dibromo-3-methyl-4-nitrophenoxy)-2-hydroxymethyl-6-isopropylphenol of Part 10A (85 mg, 0.18 mmol), Na₂S₂O₄ (467 mg, 2.68 mmol) and EtOH (2 mL) was prepared in a microwave safe reaction vial. After irradiation for 5 minutes at 170° C. a saturated aqueous solution of NaHCO₃ (5 mL) was added to the reaction mixture. The organic phase was removed in vacuo and the aqueous phase was extracted with EtOAc and the organic phase was dried over Na₂SO₄. Concentration in vacuo gave a residue that was purified on column (silica gel, gradient elution: n-heptane/EtOAc from 1:0 to 7:3) to give 18 mg (22%) of 4-(4-amino-2,6-dibromo-3-methylphenoxy)-2-hydroxymethyl-6-isopropylphenol as a light yellow foam.

10C.

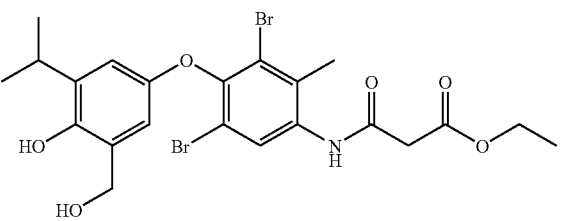

To a stirred solution of 4-(4-amino-2,6-dibromo-3-methylphenoxy)-2-hydroxymethyl-6-isopropylphenol of Part 10B (18 mg, 0.04 mmol), ethylmalonylchloride (5.7 μl, 0.044 mmol) and THF (0.5 mL) was added Et₃N (11 μl, 0.08 mmol). After 2 hours stirring at room temperature, the reaction mixture was quenched by NH₄Cl (saturated aqueous solution) and the organic phase removed in vacuo. The aqueous phase was extracted with CHCl₃ and the resulting two phases were separated with a phase separator (IST). Concentration gave 22 mg (98%) of N-[3,5-dibromo-4-[4-hydroxy-3-hydroxymethyl-5-isopropylphenoxy]-2-methylphenyl]malonamic acid ethyl ester as a yellow foam.

10 D.

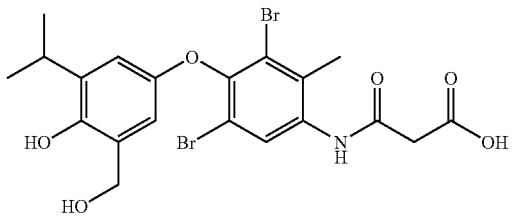

To a stirred solution of N-[3,5-dibromo-4-[4-hydroxy-3-hydroxymethyl-5-isopropylphenoxy]-2-methylphenyl]malonamic acid ethyl ester of Part 10C (22 mg, 0.039 mmol) and THF (0.5 mL) was added LiOH (0.5 mL, 1N). After 1 hour stirring at room temperature, 1N HCl was added until pH reached 1. Extraction with EtOAc, drying over Na₂SO₄ and concentration gave a residue that was purified by preparative HPLC (C₈, MeCN/water/formic acid, gradient elution from 5:95:0.5 to 70:30:0.2). This gave N-[3,5-dibromo-4-[4-hydroxy-3-hydroxymethyl-5-isopropylphenoxy]-2-methylphenyl]malonamic acid as a white solid (4 mg, 19%).

HPLC: YMC Pro C-8 reversed phase (2.1×50 mm),5 to 100% solvent B over 5 min, 1 ml/min, 3 min hold time, Solvent A=0.05% Formic acid in water, Solvent B=MeCN, retention time=3.62 min. LCMS found 526, 528.2, 530.0 (M−H)⁻.

EXAMPLE 11

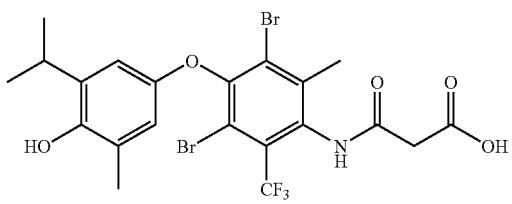

N-[3,5-dibromo-4-[4-hydroxy-5-isopropyl-3-methylphenoxy]-2-trifluoromethylphenyl]-malonamic acid

11A.

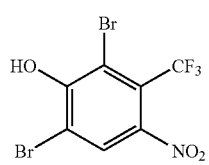

2-Nitro-5-hydroxybenzotrifluoride (2.0 g, 9.7 mmol) was dissolved in a mixture of MeOH and CH₂Cl₂ (80 mL, 1:1) at 0° C. Benzyltrimethylammoniumtribromide (7.53 g, 19.3 mmol) and CaCO₃ (2.0 g, 19.3 mmol) was added. The reaction mixture was heated at reflux for three days. The reaction was deemed complete by HPLC and LC/MS analysis and quenched by the addition of 1N HCl. The reaction mixture was washed with brine, dried with MgSO₄ and purified on column (silica gel, with gradient elution of CHCl₃/MeOH). This gave to 550 mg (16%) of 2,6-dibromo-3-trifluoromethyl-4-nitrophenol.

11B.

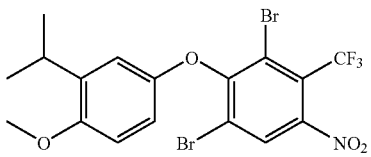

A solution of bis(3-isopropyl-4-methoxyphenyl)iodonium tetrafluroborate (1.2 g , 2.3 mmol) and copper powder (192 mg, 3.01 mmol) in dichloromethane was stirred at room temperature. After 15 minutes 2,6-dibromo-3-trifluoromethyl-4-nitrophenol of Part 11A (550 mg, 1.51 mmol) and Et₃N (304 mg, 3.01 mmol) was added. The reaction was heated at reflux for three days. The reaction was monitored by TLC (n-heptane/EtOAc 65:35) and when complete the reaction mixture was filtrated and concentrated. The residue was purified on column chromatography (silica gel, with gradient elution with n-heptane/EtOAc) to give 450 mg (58%) of 4-(2,6-dibromo-4-nitro-3-trifluoromethylphenoxy)-2-isopropylanisole.

11C.

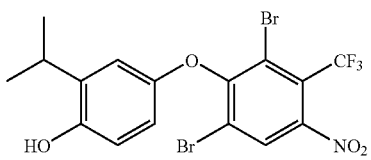

To a solution of 44-(2,6-dibromo-4-nitro-3-trifluoromethyl-phenoxy)-2-isopropylanisole of Part 11B (390 mg , 0.80 mmol) in CH₂Cl₂ (50 mL), BF₃.Me₂S (2 mL) was added drop-wise at 0° C. The reaction mixture was stirred overnight at room temperature. The reaction progress was monitored by TLC (n-heptane/EtOAc 65:35) and when the reaction was complete, the reaction mixture was washed with water, brine, the organic layer dried over MgSO₄ and concentrated. The residue was purified on column (silica gel, gradient elution with n-heptane/EtOAc) to give 224 mg (56%) of 4-(2,6-dibromo-4-nitro-3-trifluoromethylphenoxy)-2-isopropylphenol.

11D.

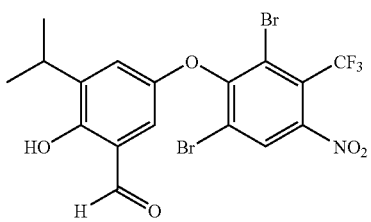

4-(2,6-dibromo-4-nitro-3-trifluoromethylphenoxy)-2-isopropylphenol of Part 11C (220 mg, 0.44 mmol) was dissolved in TFA (3 mL) and hexamethylenetetramine (154 mg, 1.1 mmol) was added to the reaction. The reaction mixture was heated at 98° C. for 12 hours, cooled down and 1N HCl (4 mL) was added. The reaction mixture was stirred for 5 hours at room temperature, extracted with EtOAc, washed with $H_2O$, $NaHCO_3$ and brine. The organic layer was dried by $MgSO_4$ and concentrated. The residue was purified on column (silica gel, gradient elution with n-heptane/EtOAc) to give 130 mg (57%) of 5-(2,6-dibromo-4-nitro-3-trifluoromethylphenoxy)-2-hydroxy-3-isopropylbenzaldehyde.
11E.

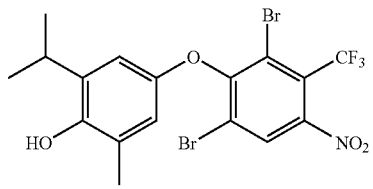

Triethylsilane (115 mg, 0.99 mmol) was added to 5-(2,6-dibromo-4-nitro-3-trifluoromethylphenoxy)-2-hydroxy-3-isopropylbenzaldehyde of Part 11D (130 mg, 0.25 mmol) and stirred at room temperature for two minutes. TFA (6 mL) was added and the reaction mixture was stirred at room temperature for 16 hours. The reaction mixture was concentrated and the residue was purified on column (silica gel, gradient elution with n-heptane/EtOAc) to give 133 mg (99%) of 4-(2,6-dibromo-4-nitro-3-trifluoromethylphenoxy)-2-methyl-6-isopropylphenol.
11F.

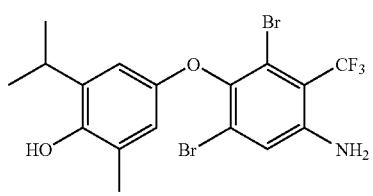

4-(2,6-Dibromo-4-nitro-3-trifluoromethylphenoxy)-2-methyl-6-isopropylphenol of Part 11E (120 mg, 0.23 mmol) was dissolved in EtOH (5 mL) and sodium hydrosulfite (204 mg, 1.2 mmol) was added. The reaction mixture was heated at reflux for 48 hours. The reaction progress was monitored by TLC (n-heptane/EtOAc 65:35) and when complete diluted with EtOAc. The organic phase was washed with water, brine, dried over $MgSO_4$ and concentrated. The residue was purified on column (silica gel, gradient elution with n-heptane/EtOAc) to give 90 mg (81%) of 4-(4-amino-2,6-dibromo-3-trifluoromethylphenoxy)-2-methyl-6-isopropylphenol.
11G.

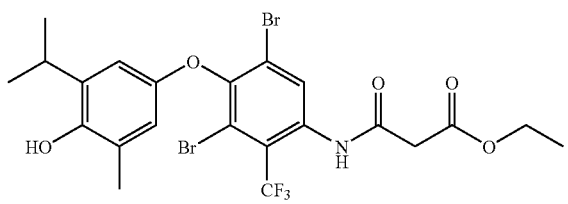

A solution of diethyl malonate (0.50 mL) and 4-(4-amino-2,6-dibromo-3-trifluoromethylphenoxy)-2-methyl-6-isopropylphenol of Part 11F (20 mg, 0.04 mmol) was heated for 5 minutes at 140° C. and subsequently for 10 minutes at 180° C. in a micro oven (Emrys Optimizer, Personal Chemistry). Filtration through a pad of silica gave a light yellow residue, which was dissolved in THF (0.5 mL) and treated with 1N LiOH (0.50 mL) for 1 hour. The reaction mixture was acidified with 1N HCl and extracted with EtOAc. The combined organic layers were dried over $Na_2SO_4$ and concentrated in vacuo. The residue was purified on preparative HPLC ($C_8$, MeCN/$H_2O$/formic acid, gradient elution from 5:95:0.5 to 70:30:0.2). This gave 5 mg (22 %) of N-[3,5-dibromo-4-[4-hydroxy-5-isopropyl-3-methylphenoxy]-2-trifluoromethyl-phenyl]-malonamic acid ethyl ester. LC-MS (ES-1): m/z 566.
11H.

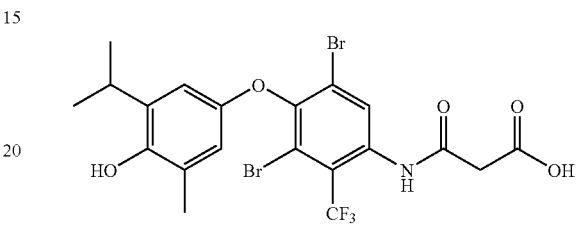

To a stirred solution of compound N-[3,5-dibromo-4-[4-hydroxy-5-isopropyl-3-methylphenoxy]-2-trifluoromethyl-phenyl]malonamic acid ethyl ester of Part 11 G (15 mg, 0.027 mmol) in THF (0.5 mL) was added LiOH (0.25 mL, 1N). After 1 hour stirring the pH of reaction was adjusted to 1 by 1N HCl and the organic phase was removed in vacuo. The resulting mixture was extracted with EtOAc (3×3 mL) and the combined organic phases were dried over $Na_2SO_4$ before concentration in vacuo. The residue was purified on column (silica gel, gradient elution, $CHCl_3$/MeOH/AcOH from 1:0:0 to 90:10:1) to give N-[3,5-dibromo-4-[4-hydroxy-5-isopropyl-3-methylphenoxy]-2-trifluoromethylphenyl]malonamic acid as a white solid (6 mg, 42%)
δ1H NMR (500 MHz, CD3OD) δ 8.15 (s, 1H), 6.5 (d, 1H), 6.3 (d, 1H), 3.4 (s, 2H), 3.2 (septet, 1H), 2.17 (s, 3H), 1.15 (d, 6H). HPLC: YMC Pro C-8 reversed phase (2.1×50 mm),5 to 100% solvent B over 5 min, 1 ml/min, 3 min hold time, Solvent A=0.05% Formic acid in water, Solvent B=MeCN, retention time=3.94 min. LCMS found 566.3, 568.1, 570. (M−H)⁻.

It should be understood that while this invention has been described herein in terms of specific embodiments set forth in detail, such embodiments are presented by way of illustration of the general principles of the invention, and the invention is not necessarily limited thereto. Certain modifications and variations in any given material, process step or chemical formula will be readily apparent to those skilled in the art without departing from the true spirit and scope of the present invention, and all such modifications and variations should be considered within the scope of the claims that follow.

What is claimed is:
1. A compound having the following Formula I:

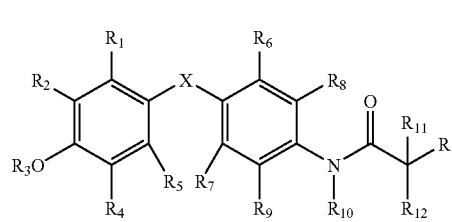

wherein
X is selected from oxygen (—O—), selenium (—Se—), sulfur (—S—), sulfenyl (SO), sulfonyl ($SO_2$), carbonyl (—CO—), methylene (—$CH_2$—) and —NH—;
$R_1$ is hydrogen;
$R_2$ is $C_1$ to $C_6$ alkyl or $C_3$ to $C_7$ cycloalkyl;
$R_3$ is hydrogen;
$R_4$ is $C_1$ to $C_4$ alkyl
$R_5$ is hydrogen;
$R_6$ and $R_7$ are independently bromo, chloro or methyl;
$R_8$ is halogen or $C_1$ to $C_4$ alkyl;
$R_9$ is hydrogen or halogen;
$R_{10}$ is hydrogen;
$R_{11}$ is carboxyl;
$R_{12}$ is hydrogen; and
$R_{13}$ is hydrogen.

2. The compound as defined in claim 1 wherein $R_2$ is isopropyl.

3. The compound as defined in claim 1 wherein
$R_1$ is hydrogen;
$R_2$ is isopropyl;
$R_3$ is hydrogen;
$R_4$ is $C_1$ to $C_4$ alkyl;
$R_5$ is hydrogen;
$R_6$ and $R_7$ are independently bromo, chloro or methyl;
$R_8$ is halogen or methyl;
$R_9$ is hydrogen or chloro;
$R_{10}$ is hydrogen;
$R_{11}$ is carboxyl;
$R_{12}$ is hydrogen; and
$R_{13}$ is hydrogen.

4. The compound as defined in claim 1 wherein
$R_1$ is hydrogen;
$R_2$ is isopropyl;
$R_3$ is hydrogen;
$R_4$ is methyl;
$R_5$ is hydrogen;
$R_6$ and $R_7$ are independently bromo or chloro;
$R_8$ is chloro or methyl;
$R_9$ is hydrogen;
$R_{10}$ is hydrogen;
$R_{11}$ is carboxyl;
$R_{12}$ is hydrogen; and
$R_{13}$ is hydrogen.

5. The compound as defined in claim 1 having the structure

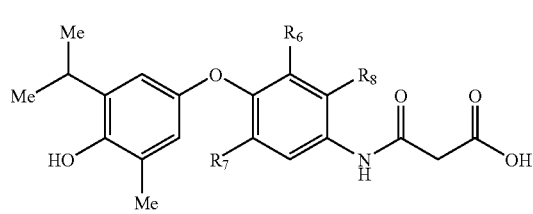

or

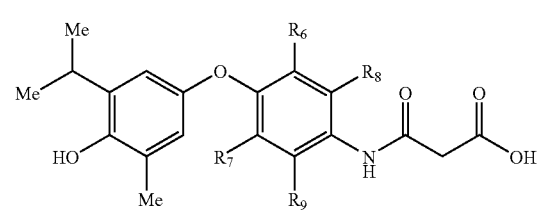

or an alkyl ester thereof.

6. The compound as defined in claim 1 having the structure

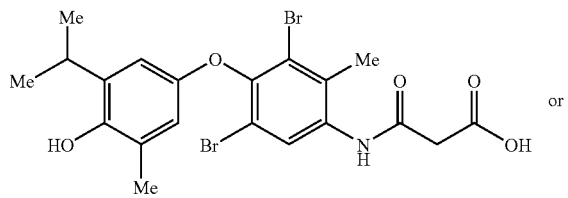

or

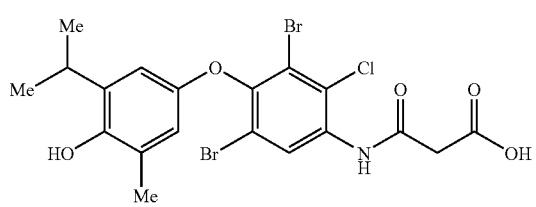

or

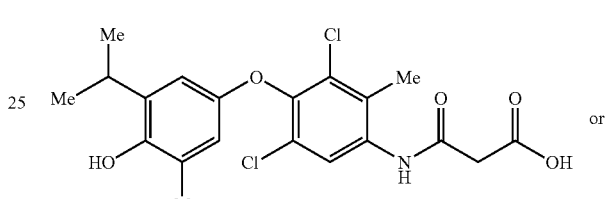

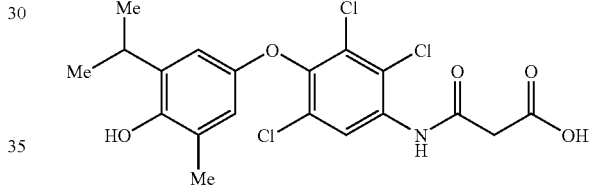

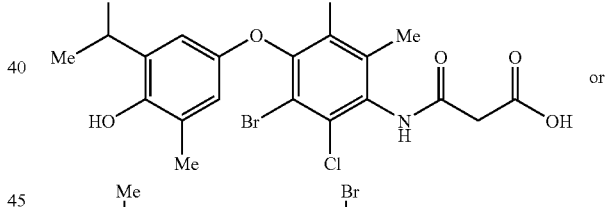

or

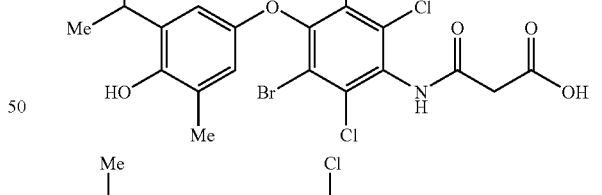

or

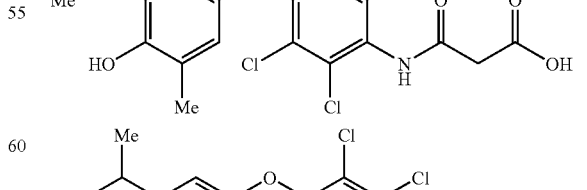

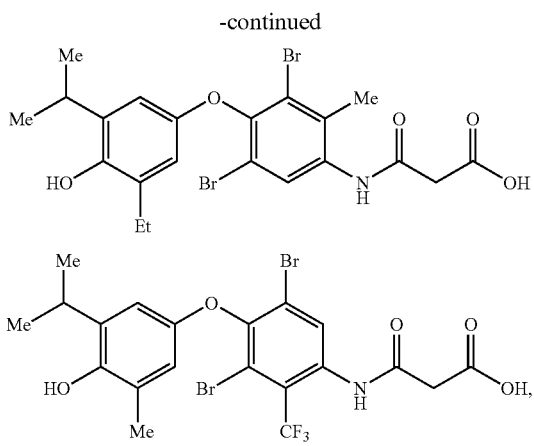

or an alkyl ester thereof.

7. The compound as defined in claim 1 having the structure

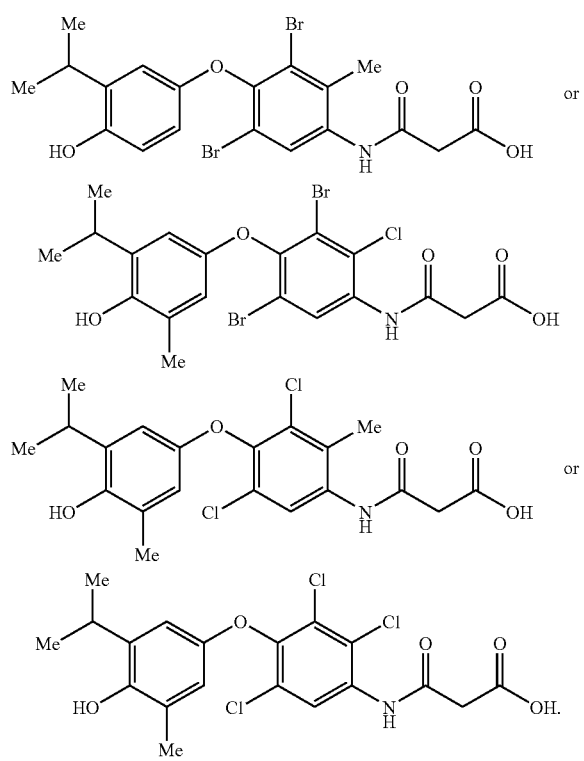

8. The compound as defined in claim 1 having the structure

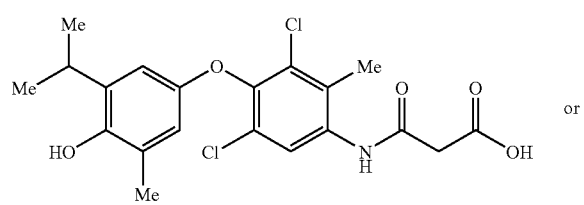

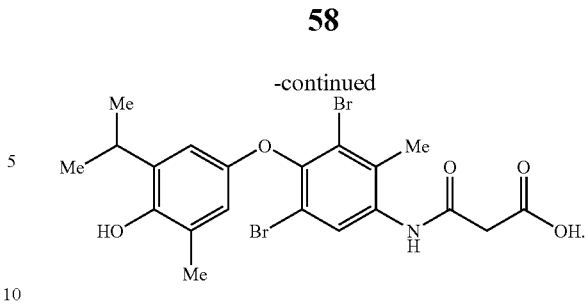

9. A pharmaceutical composition comprising a compound as defined in claim 1 and a pharmaceutically acceptable carrier therefor.

10. The pharmaceutical composition of claim 9 further comprising at least one additional therapeutic agent selected from other compounds of formula I, anti-diabetic agents, anti-osteoporosis agents, anti-obesity agents, growth promoting agents, anti-inflammatory agents, anti-anxiety agents, anti-depressants, anti-hypertensive agents, cardiac glycosides, cholesterol/lipid lowering agents, appetite supressants, bone resorption inhibitors, thyroid mimetics, anabolic agents, anti-tumor agents and retinoids.

11. The pharmaceutical composition of claim 10 wherein said additional therapeutic agent is an antidiabetic agent selected from a biguanide, a glucosidase inhibitor, a meglitinide, a sulfonylurea, a thiazolidinedione, a PPAR-alpha agonist, a PPAR-gamma agonist, a PPAR alpha/gamma dual agonist, an SGLT2 inhibitor, a glycogen phosphorylase inhibitor, an aP2 inhibitor, a glucagon-like peptide-1 (GLP-1), a dipeptidyl peptidase IV inhibitor and insulin.

12. The pharmaceutical composition of claim 10 wherein said additional therapeutic agent is an antidiabetic agent selected from metformin, glyburide, glimepiride, glipyride, glipizide, chlorpropamide, gliclazide, acarbose, miglitol, troglitazone, pioglitazone, englitazone, darglitazone, rosiglitazone and insulin.

13. The pharmaceutical composition of claim 10 wherein said additional therapeutic agent is an anti-obesity agent selected from an aP2 inhibitor, a PPAR gamma antagonist, a PPAR delta agonist, a beta 3 adrenergic agonist, a lipase inhibitor, a serotonin reuptake inhibitor, a cannabinoid-1 receptor antagonist and an anorectic agent.

14. The pharmaceutical composition of claim 10 wherein said additional therapeutic agent is a hypolipidemic agent selected from thiazolidinedione, an MTP inhibitor, a squalene synthetase inhibitor, an HMG CoA reductase inhibitor, a fibric acid derivative, an ACAT inhibitor, a cholesterol absorption inhibitor, an ileal $Na^+$/bile cotransporter inhibitor, a bile acid sequestrant and a nicotinic acid or a derivative thereof.

15. A method for activating thyroid receptor beta in a disease associated with metabolic dysfunction, or which is dependent on the expression of a $T_3$ regulated gene, which comprises administering to a mammalian patient in need of treatment a therapeutically effective amount of a compound as defined in claim 1.

16. A method for activating thyroid receptor beta in a disease selected from the group consisting of obesity, hypercholesterolemia, atherosclerosis, depression, osteoporosis, hypothyroidism, subclinical hyperthyroidism, non-toxic goiter, reduced bone mass, density or growth, eating disorders, reduced cognitive function, thyroid cancer, glaucoma, cardiac arrhythmia, congestive heart failure or a skin disorder or disease, which comprises administering to mammalian patient in need of treatment a therapeutically effective amount of a compound as defined in claim 1.

17. The method according to claim 16 wherein the skin disorder or disease is dermal atrophy, post surgical bruising caused by laser resurfacing, keloids, stria, cellulite, roughened skin, actinic skin damage, lichen planus, ichtyosis, acne, psoriasis, Dernier's disease, eczema, atopic dermatitis, chloracne, pityriasis or skin scarring.

18. The method according to claim 16 further comprising administering, concurrently or sequentially, a therapeutically effective amount of at least one additional therapeutic agent selected from other compounds of formula I, anti-diabetic agents, anti-osteoporosis agents, anti-obesity agents, growth promoting agents, anti-inflammatory agents, anti-anxiety agents, anti-depressants, anti-hypertensive agents, cardiac glycosides, cholesterol/lipid lowering agents, appetite supressants, bone resorption inhibitors, thyroid mimetics, anabolic agents, anti-tumor agents and retinoids.

19. A method of activating thyroid receptor beta in a skin disorder or disease which comprises administering to a mammalian patient a therapeutically effective amount of a compound as defined in claim 1 in combination with a retinoid or a vitamin D analog.

20. A method for treating or delaying the progression or onset of obesity which comprises administering to mammalian patient in need of treatment a therapeutically effective amount of a compound as defined in claim 1.

21. A method according to claim 20 further comprising administering, concurrently or sequentially, a therapeutically effective amount of at least one additional therapeutic agent selected from an anti-obesity agent or an appetite suppressant.

22. A method according to claim 21 wherein said anti-obesity agent is selected from aP2 inhibitors, PPAR gamma antagonists, PPAR delta agonists, beta 3 adrenergic agonists, lipase inhibitors, serotonin (and dopamine) reuptake inhibitors, cannabinoid-1 receptor antagonists, other thyroid receptor agents and anorectic agents.

23. A pharmaceutical composition which functions as a selective agonist of the thyroid hormone receptor comprising a compound as defined in claim 1.

* * * * *

UNITED STATES PATENT AND TRADEMARK OFFICE
CERTIFICATE OF CORRECTION

PATENT NO.        : 7,342,127 B2                                    Page 1 of 1
APPLICATION NO. : 10/763878
DATED             : March 11, 2008
INVENTOR(S)       : William N. Washburn et al.

It is certified that error appears in the above-identified patent and that said Letters Patent is hereby corrected as shown below:

Col. 55, line 8, after "alkyl", insert -- ; --.

Col. 57, lines 3 to 9, after first structure, insert -- or --.

Col. 57, lines 26 to 31, change

"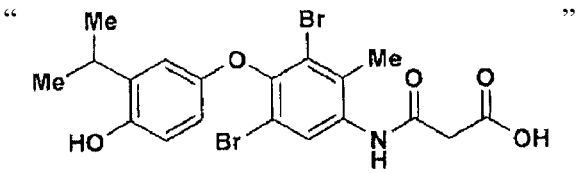"

to

-- 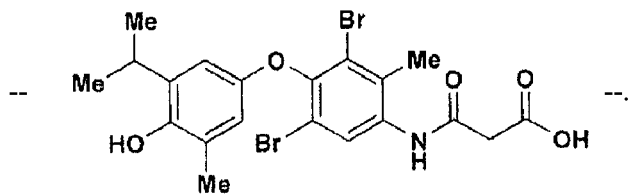 --.

Signed and Sealed this

Twelfth Day of August, 2008

JON W. DUDAS
*Director of the United States Patent and Trademark Office*